United States Patent
Endo et al.

(10) Patent No.: US 12,018,095 B2
(45) Date of Patent: *Jun. 25, 2024

(54) CELL PENETRATING PEPTIDE

(71) Applicants: Astellas Pharma Inc., Tokyo (JP); National Center for Global Health and Medicine, Tokyo (JP); Hiroshima University, Higashihiroshima (JP)

(72) Inventors: Hideki Endo, Tokyo (JP); Yukihito Ishizaka, Tokyo (JP); Akira Ishiguro, Tokyo (JP); Tomoki Takashina, Tokyo (JP); Takashi Yamamoto, Hiroshima (JP); Tetsushi Sakuma, Hiroshima (JP)

(73) Assignees: Astellas Pharma Inc., Tokyo (JP); National Center for Global Health and Medicine, Tokyo (JP); Hiroshima University, Hiroshima (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/854,647

(22) Filed: Jun. 30, 2022

(65) Prior Publication Data

US 2022/0356207 A1    Nov. 10, 2022

Related U.S. Application Data

(62) Division of application No. 16/771,009, filed as application No. PCT/JP2018/045228 on Dec. 10, 2018, now Pat. No. 11,414,456.

(30) Foreign Application Priority Data

Dec. 11, 2017 (JP) ................. 2017-236660

(51) Int. Cl.
*C07K 7/06* (2006.01)
(52) U.S. Cl.
CPC .................... *C07K 7/06* (2013.01)

(58) Field of Classification Search
None
See application file for complete search history.

(56) References Cited

U.S. PATENT DOCUMENTS

| 11,390,652 B2* | 7/2022 | Endo .............. C12N 9/22 |
| 11,414,456 B2* | 8/2022 | Endo .............. C07K 7/06 |
| 2010/0203611 A1 | 8/2010 | Ishizaka et al. |
| 2012/0252719 A1 | 10/2012 | Zhang et al. |
| 2019/0330280 A1 | 10/2019 | Endo et al. |

FOREIGN PATENT DOCUMENTS

| JP | 2014-508763 A | 4/2014 |
| WO | WO-2008/108505 A1 | 9/2008 |
| WO | WO-2012/116203 A1 | 8/2012 |
| WO | WO-2018/110471 A1 | 6/2018 |

OTHER PUBLICATIONS

Gonzalez ME ('The HIV-1 Vpr Protein: A multifaceted target for therapeutic intervention' International Journal of Molecular Sciences v18(126) 2017 pp. 1-21) (Year: 2017).

Peptide Design, Thermo Fisher Scientific, Jul. 25, 2017, retrieved on Jan. 31, 2019, with partial English translation of indicated portion.

Ramsey et al., "Cell-penetrating peptides transport therapeutics into cells," Pharmacology & Therapeutics, 2015, 154:78-86.

* cited by examiner

*Primary Examiner* — Ronald T Niebauer
(74) *Attorney, Agent, or Firm* — Foley & Lardner LLP

(57) ABSTRACT

An object of the present invention is to provide a cell penetrating peptide having a penetrating ability into cells. The present inventors provided a cell penetrating peptide consisting of the amino acid sequence of SEQ ID NO: 1, a cell penetrating peptide consisting of the amino acid sequence of SEQ ID NO: 2 and a cell penetrating peptide consisting of the amino acid sequence of SEQ ID NO: 3; and a complex comprising any one of the cell penetrating peptide and a functional molecule.

1 Claim, 3 Drawing Sheets

Specification includes a Sequence Listing.

[Figure 1]
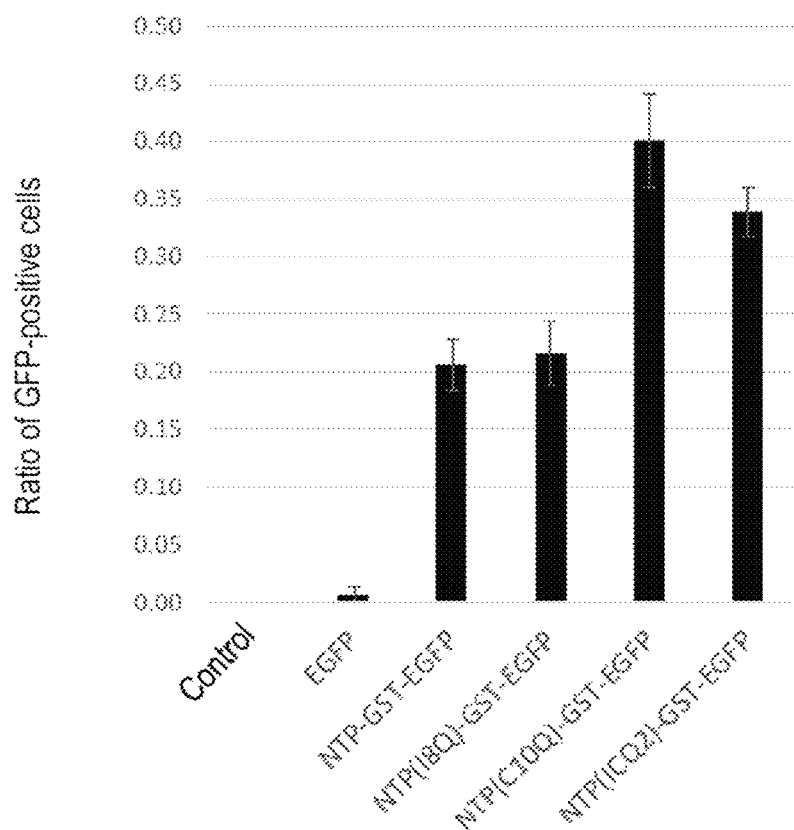

[Figure 2]
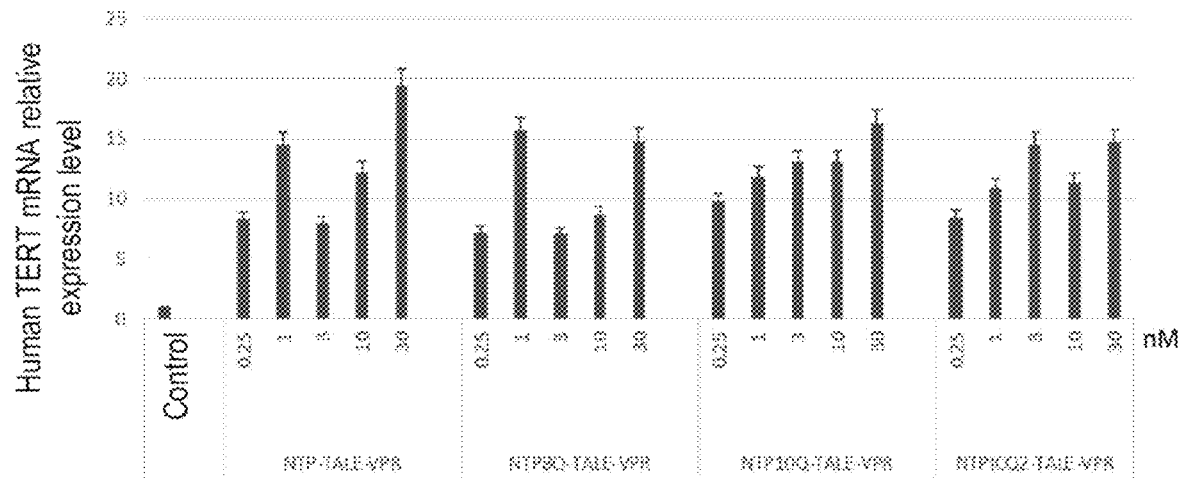
[Figure 3]
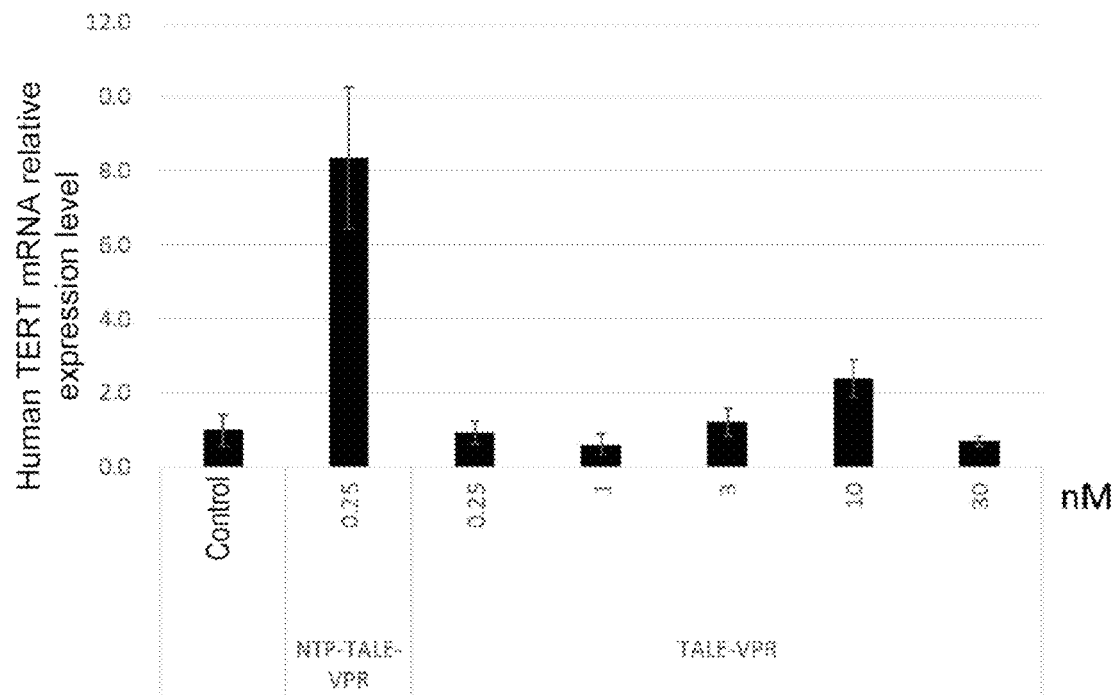

[Figure 4A]
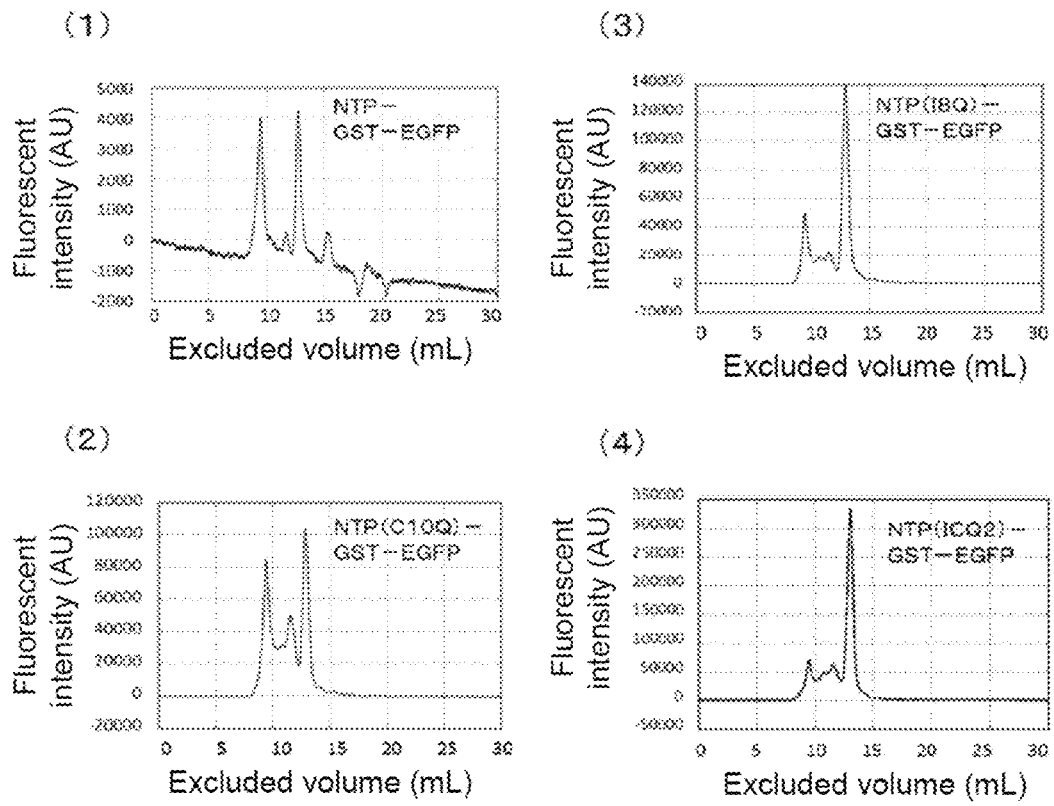
[Figure 4B]
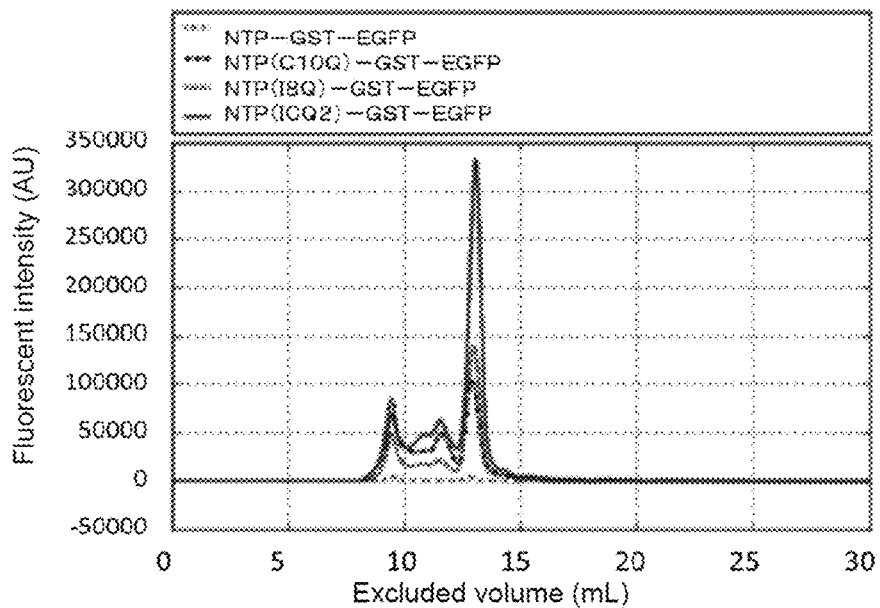

SEQUENCE LISTING

```
<160> NUMBER OF SEQ ID NOS: 41

<210> SEQ ID NO 1
<211> LENGTH: 10
<212> TYPE: PRT
<213> ORGANISM: Artificial Sequence
<220> FEATURE:
<223> OTHER INFORMATION: NTP(ICQ2)

<400> SEQUENCE: 1

Arg Ile Phe Ile His Phe Arg Gln Gly Gln
1               5                   10

<210> SEQ ID NO 2
<211> LENGTH: 10
<212> TYPE: PRT
<213> ORGANISM: Artificial Sequence
<220> FEATURE:
<223> OTHER INFORMATION: NTP(I8Q)

<400> SEQUENCE: 2

Arg Ile Phe Ile His Phe Arg Gln Gly Cys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: NTP(C10Q)

<400> SEQUENCE: 3

Arg Ile Phe Ile His Phe Arg Ile Gly Gln
1               5                   10

<210> SEQ ID NO 4
<211> LENGTH: 10
<212> TYPE: PRT
<213> ORGANISM: Artificial Sequence
<220> FEATURE:
<223> OTHER INFORMATION: NTP

<400> SEQUENCE: 4

Arg Ile Phe Ile His Phe Arg Ile Gly Cys
1               5                   10

<210> SEQ ID NO 5
<211> LENGTH: 476
<212> TYPE: PRT
```

<213> ORGANISM: Artificial Sequence
<220> FEATURE:
<223> OTHER INFORMATION: NTP-GST-EGFP

<400> SEQUENCE: 5

```
Met Arg Ile Phe Ile His Phe Arg Ile Gly Cys Ser Pro Ile Leu Gly
1               5                   10                  15

Tyr Trp Lys Ile Lys Gly Leu Val Gln Pro Thr Arg Leu Leu Leu Glu
            20                  25                  30

Tyr Leu Glu Glu Lys Tyr Glu Glu His Leu Tyr Glu Arg Asp Glu Gly
        35                  40                  45

Asp Lys Trp Arg Asn Lys Lys Phe Glu Leu Gly Leu Glu Phe Pro Asn
    50                  55                  60

Leu Pro Tyr Tyr Ile Asp Gly Asp Val Lys Leu Thr Gln Ser Met Ala
65              70                  75                  80

Ile Ile Arg Tyr Ile Ala Asp Lys His Asn Met Leu Gly Gly Cys Pro
                85                  90                  95

Lys Glu Arg Ala Glu Ile Ser Met Leu Glu Gly Ala Val Leu Asp Ile
            100                 105                 110

Arg Tyr Gly Val Ser Arg Ile Ala Tyr Ser Lys Asp Phe Glu Thr Leu
        115                 120                 125

Lys Val Asp Phe Leu Ser Lys Leu Pro Glu Met Leu Lys Met Phe Glu
    130                 135                 140

Asp Arg Leu Cys His Lys Thr Tyr Leu Asn Gly Asp His Val Thr His
145                 150                 155                 160

Pro Asp Phe Met Leu Tyr Asp Ala Leu Asp Val Val Leu Tyr Met Asp
                165                 170                 175

Pro Met Cys Leu Asp Ala Phe Pro Lys Leu Val Cys Phe Lys Lys Arg
            180                 185                 190

Ile Glu Ala Ile Pro Gln Ile Asp Lys Tyr Leu Lys Ser Ser Lys Tyr
        195                 200                 205

Ile Ala Trp Pro Leu Gln Gly Trp Gln Ala Thr Phe Gly Gly Gly Asp
    210                 215                 220

His Pro Pro Lys Ser Asp Leu Glu Val Leu Phe Gln Gly Pro Val Ser
225                 230                 235                 240

Lys Gly Glu Glu Leu Phe Thr Gly Val Val Pro Ile Leu Val Glu Leu
                245                 250                 255

Asp Gly Asp Val Asn Gly His Lys Phe Ser Val Ser Gly Glu Gly Glu
            260                 265                 270

Gly Asp Ala Thr Tyr Gly Lys Leu Thr Leu Lys Phe Ile Cys Thr Thr
        275                 280                 285

Gly Lys Leu Pro Val Pro Trp Pro Thr Leu Val Thr Thr Leu Thr Tyr
    290                 295                 300

Gly Val Gln Cys Phe Ser Arg Tyr Pro Asp His Met Lys Gln His Asp
305                 310                 315                 320

Phe Phe Lys Ser Ala Met Pro Glu Gly Tyr Val Gln Glu Arg Thr Ile
                325                 330                 335

Phe Phe Lys Asp Asp Gly Asn Tyr Lys Thr Arg Ala Glu Val Lys Phe
            340                 345                 350

Glu Gly Asp Thr Leu Val Asn Arg Ile Glu Leu Lys Gly Ile Asp Phe
        355                 360                 365

Lys Glu Asp Gly Asn Ile Leu Gly His Lys Leu Glu Tyr Asn Tyr Asn
    370                 375                 380

Ser His Asn Val Tyr Ile Met Ala Asp Lys Gln Lys Asn Gly Ile Lys
```

```
                385                 390                 395                 400
Val Asn Phe Lys Ile Arg His Asn Ile Glu Asp Gly Ser Val Gln Leu
                    405                 410                 415

Ala Asp His Tyr Gln Gln Asn Thr Pro Ile Gly Asp Gly Pro Val Leu
                420                 425                 430

Leu Pro Asp Asn His Tyr Leu Ser Thr Gln Ser Ala Leu Ser Lys Asp
                    435                 440                 445

Pro Asn Glu Lys Arg Asp His Met Val Leu Leu Glu Phe Val Thr Ala
                450                 455                 460

Ala Gly Ile Thr Leu Gly Met Asp Glu Leu Tyr Lys
465                 470                 475

<210> SEQ ID NO 6
<211> LENGTH: 1445
<212> TYPE: DNA
<213> ORGANISM: Artificial Sequence
<220> FEATURE:
<223> OTHER INFORMATION: KpnI-NTP-GST-EGFP-NotI

<400> SEQUENCE: 6
ggtaccatgc ggatcttcat ccacttccgg atcggctgct ccctatact aggttattgg        60 aaaattaagg gccttgtgca acccactcga cttcttttgg aatatcttga agaaaaatat      120
gaagagcatt tgtatgagcg cgatgaaggt gataaatggc gaaacaaaaa gtttgaattg      180
ggtttggagt ttcccaatct tccttattat attgatggtg atgttaaatt aacacagtct      240
atggccatca tacgttatat agctgacaag cacaacatgt tgggtggttg tccaaaagag      300
cgtgcagaga tttcaatgct tgaaggagcg gttttggata ttagatacgg tgtttcgaga      360
attgcatata gtaaagactt tgaaactctc aaagttgatt tcttagcaa gctacctgaa       420 atgctgaaaa tgttcgaaga tcgtttatgt cataaaacat atttaaatgg tgatcatgta      480
acccatcctg acttcatgtt gtatgacgct cttgatgttg ttttatacat ggacccaatg      540
tgcctggatg cgttcccaaa attagtttgt tttaaaaaac gtattgaagc tatcccacaa      600
attgataagt acttgaaatc cagcaagtat atagcatggc cttttgcaggg ctggcaagcc    660 acgtttggtg gtggcgacca tcctccaaaa tcggatctgg aagttctgtt ccaggggccc      720
gtgtccaagg gcgaggaact gttcacaggc gtggtgccca tcctggtgga actggacggg      780
gatgtgaacg gccacaagtt cagcgtgtcc ggcgagggcg aaggcgacgc cacatatggc      840
aagctgaccc tgaagttcat ctgcaccacc ggcaagctgc ccgtgccttg gcctaccctc      900
gtgaccacac tgacctacgg cgtgcagtgc ttcagcagat accccgacca tatgaagcag      960
cacgacttct tcaagagcgc catgcccgag ggctacgtgc aggaacggac catcttcttt     1020
aaggacgacg gcaactacaa gaccaggggc gaagtgaagt cgagggcga caccctcgtg     1080 aaccggatcg agctgaaggg catcgacttc aaagaggacg gcaacatcct gggccacaag     1140
ctggagtaca actacaacag ccacaacgtg tacatcatgg ccgacaagca gaaaaacggc     1200
atcaaagtga acttcaagat ccggcacaac atcgaggacg gctccgtgca gctggccgac     1260
cactaccagc agaacacccc catcggagat ggccccgtgc tgctgcccga caaccactac     1320
ctgagcacac agagcgccct gagcaaggac cccaacgaga gcgggacca tatggtgctg      1380 ctggaattcg tgaccgccgc tggcatcacc ctgggcatgg acgagctgta caagtgagcg     1440
gccgc                                                                  1445

<210> SEQ ID NO 7
```

<211> LENGTH: 1428
<212> TYPE: DNA
<213> ORGANISM: Artificial Sequence
<220> FEATURE:
<223> OTHER INFORMATION: NTP-GST-EGFP

<400> SEQUENCE: 7

```
atgcggatct tcatccactt ccggatcggc tgctccccta tactaggtta ttggaaaatt        60
aagggccttg tgcaacccac tcgacttctt ttggaatatc ttgaagaaaa atatgaagag       120
catttgtatg agcgcgatga aggtgataaa tggcgaaaca aaaagtttga attgggtttg       180
gagtttccca atcttcctta ttatattgat ggtgatgtta aattaacaca gtctatggcc       240
atcatacgtt atatagctga caagcacaac atgttgggtg ttgtccaaa agagcgtgca       300
gagatttcaa tgcttgaagg agcggttttg gatattagat acggtgtttc gagaattgca       360
tatagtaaag actttgaaac tctcaaagtt gattttctta gcaagctacc tgaaatgctg       420
aaaatgttcg aagatcgttt atgtcataaa acatatttaa atggtgatca tgtaacccat       480
cctgacttca tgttgtatga cgctcttgat gttgttttat acatggaccc aatgtgcctg       540
gatgcgttcc caaaattagt ttgttttaaa aacgtattg aagctatccc acaaattgat       600
aagtactga atccagcaa gtatatagca tggccttttgc agggctggca agccacgttt      660
ggtggtggcg accatcctcc aaaatcggat ctggaagttc tgttccaggg gcccgtgtcc       720
aagggcgagg aactgttcac aggcgtggtg cccatcctgg tggaactgga cggggatgtg       780
aacggccaca gttcagcgt gtccggcgag ggcgaaggcg acgccacata tggcaagctg       840
accctgaagt tcatctgcac caccggcaag ctgcccgtgc cttggcctac cctcgtgacc       900
acactgacct acggcgtgca gtgcttcagc agataccccg accatatgaa gcagcacgac       960
ttcttcaaga cgccatgcc cgagggctac gtgcaggaac ggaccatctt ctttaaggac      1020
gacggcaact acaagaccag gccgaagtg aagttcgagg gcgacaccct cgtgaaccgg      1080
atcgagctga aggggcatcga cttcaaagag gacggcaaca tcctgggcca caagctggag      1140
tacaactaca acagccacaa cgtgtacatc atggccgaca gcagaaaaa cggcatcaaa      1200
gtgaacttca gatccggca caacatcgag gacggctccg tgcagctggc cgaccactac      1260
cagcagaaca cccccatcgg agatggcccc gtgctgctgc ccgacaacca ctacctgagc      1320
acacagagcg ccctgagcaa ggaccccaac gagaagcggg accacatggt gctgctggaa      1380
ttcgtgaccg ccgctggcat caccctgggc atggacgagc tgtacaag              1428
```

<210> SEQ ID NO 8
<211> LENGTH: 28
<212> TYPE: DNA
<213> ORGANISM: Artificial Sequence
<220> FEATURE:
<223> OTHER INFORMATION: Primer

<400> SEQUENCE: 8

```
tccggcaggg ctgctcccct atactagg                                            28
```

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9

```
agcagccctg ccggaagtgg atgaagatcc                                          30
```

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
atcggccagt ccctatact aggttattgg                              30

<210> SEQ ID NO 11
<211> LENGTH: 31
<212> TYPE: DNA
<213> ORGANISM: Artificial Sequence
<220> FEATURE:
<223> OTHER INFORMATION: Primer

<400> SEQUENCE: 11
aggggactgg ccgatccgga agtggatgaa g                           31

<210> SEQ ID NO 12
<211> LENGTH: 28
<212> TYPE: DNA
<213> ORGANISM: Artificial Sequence
<220> FEATURE:
<223> OTHER INFORMATION: Primer

<400> SEQUENCE: 12
tccggcaggg ccagtcccct atactagg                               28

<210> SEQ ID NO 13
<211> LENGTH: 32
<212> TYPE: DNA
<213> ORGANISM: Artificial Sequence
<220> FEATURE:
<223> OTHER INFORMATION: Primer

<400> SEQUENCE: 13
actggccctg ccggaagtgg atgaagtgga tg                          32

<210> SEQ ID NO 14
<211> LENGTH: 30
<212> TYPE: DNA
<213> ORGANISM: Artificial Sequence
<220> FEATURE:
<223> OTHER INFORMATION: NTP

<400> SEQUENCE: 14
aggatcttca tccacttccg gatcggctgc                             30

<210> SEQ ID NO 15
<211> LENGTH: 687
<212> TYPE: DNA
<213> ORGANISM: Schistosoma japonicum

<400> SEQUENCE: 15
atgtccccta tactaggtta ttggaaaatt aagggccttg tgcaacccac tcgacttctt    60
ttggaatatc ttgaagaaaa atatgaagag catttgtatg agcgcgatga aggtgataaa   120
tggcgaaaca aaagtttga attgggtttg agtttccca atcttcctta ttatattgat   180
ggtgatgtta aattaacaca gtctatggcc atcatacgtt atatagctga caagcacaac   240
atgttgggtg gttgtccaaa agagcgtgca gagatttcaa tgcttgaagg agcggttttg   300

| | | |
|---|---|---|
| gatattagat acggtgtttc gagaattgca tatagtaaag actttgaaac tctcaaagtt | 360 | |
| gattttctta gcaagctacc tgaaatgctg aaaatgttcg aagatcgttt atgtcataaa | 420 | |
| acatatttaa atggtgatca tgtaacccat cctgacttca tgttgtatga cgctcttgat | 480 | |
| gttgttttat acatggaccc aatgtgcctg gatgcgttcc caaaattagt ttgttttaaa | 540 | |
| aaacgtattg aagctatccc acaaattgat aagtacttga atccagcaa gtatatagca | 600 | |
| tggcctttgc agggctggca agccacgttt ggtggtggcg accatcctcc aaaatcggat | 660 | |
| ctggaagttc tgttccaggg gcccctg | 687 | |

<210> SEQ ID NO 16
<211> LENGTH: 21
<212> TYPE: DNA
<213> ORGANISM: Artificial Sequence
<220> FEATURE:
<223> OTHER INFORMATION: TEV

<400> SEQUENCE: 16
gaaaacctgt atttccaatc t                                        21

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
gtcacagctt gtctgtaagc g                                        21

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
aaagggcctc gtgatacgcc t                                        21

<210> SEQ ID NO 19
<211> LENGTH: 1687
<212> TYPE: DNA
<213> ORGANISM: Artificial Sequence
<220> FEATURE:
<223> OTHER INFORMATION: deltaTALE-VP64

<400> SEQUENCE: 19

| | | |
|---|---|---|
| accatgatcc acggagtccc agcagccgta gatttgagaa ctttgggata ttcacagcag | 60 | |
| cagcaggaaa agatcaagcc caaagtgagg tcgacagtcg cgcagcatca cgaagcgctg | 120 | |
| gtgggtcatg ggtttacaca tgcccacatc gtagccttgt cgcagcaccc tgcagccctt | 180 | |
| ggcacggtcg ccgtcaagta ccaggacatg attgcgcgcg tgccggaagc cacacatgag | 240 | |
| gcgatcgtcg gtgtggggaa acagtggagc ggagcccgag cgcttgaggc cctgttgacg | 300 | |
| gtcgcgggag agctgagagg gcctcccctt cagctggaca cgggccagtt gctgaagatc | 360 | |
| gcgaagcggg gaggagtcac ggcggtcgag gcggtacacg cgtggcgcaa tgcgctcacg | 420 | |
| ggagcacccc tcaaggagac gggcgccgct acagggcgcg tcccattcgc cattcaggct | 480 | |
| gcgcaactgt tggaagggc gatcggtgcg ggcctcttcg ctattacgcc agctggcgaa | 540 | |
| agggggatgt gctgcaaggc gattaagttg gtaacgcca gggttttccc agtcacgacg | 600 | |

```
ttgtaaaacg acggccagtg agcgcgcgta atacgactca ctatagggcg aattgggtac    660
cgggcccccc ctcgaggtcc tccagctttt gttcccttta gtgagggtta attgcgcgct    720
tggcgtaatc atggtcatag ctgtttcctg tgtgaaattg ttatccgctc acaattccac    780
acaacatacg agccggaagc ataaagtgta aagcctgggg tgcctaatga gtgagctaac    840
tcacattaat tgcgttgcgc tcactgcccg ctttccaccg tcgtctcca ccctgagca    900 ggtagtggct attgcatccc acgacggggg cagacccgca ctggagtcaa tcgtggccca    960
gctctcgagg ccggaccccg cgctggccgc actcactaat gatcatcttg tagcgctggc   1020
ctgcctcggc ggacgacccg ccttggatgc ggtgaagaag gggctcccgc acgcgcctgc   1080
attgattaag cggaccaaca gaaggatccc cgagaggaca tcacatcgag tggcagatca   1140
cgcgcaagtg gtccgcgtgc tcggattctt ccagtgtcac tcccacccg cacaagcgtt    1200 cgatgacgcc atgactcaat ttggtatgtc gagacacgga ctgctgcagc tctttcgtag   1260
agtcggtgtc acagaactgg aggcccgctc gggcacactg cctcccgcct ccagcggtg    1320 ggacaggatt ctccaagcga gcggtatgaa acgcgcgaag ccttcaccta cgtcaactca   1380
gacacctgac caggcgagcc ttcatgcgtt cgcagactcg ctggagaggg atttggacgc   1440
gccctcgccc atgcatgaag gggaccaaac tcgcgcgtca gccagcccca agaagaagag   1500
aaaggtggag ccagcggtt ccggacgggc tgacgcattg gacgattttg atctggatat    1560
gctgggaagt gacgccctcg atgattttga ccttgacatg cttggttcgg atgcccttga   1620
tgactttgac ctcgacatgc tcggcagtga cgcccttgat gatttcgacc tggacatgct   1680
ggtttaa                                                             1687
```

<210> SEQ ID NO 20
<211> LENGTH: 18
<212> TYPE: DNA
<213> ORGANISM: Homo sapiens

<400> SEQUENCE: 20
tcagagggac gcagtctt                                                   18

<210> SEQ ID NO 21
<211> LENGTH: 50
<212> TYPE: PRT
<213> ORGANISM: Artificial Sequence
<220> FEATURE:
<223> OTHER INFORMATION: VP64

<400> SEQUENCE: 21

Asp Ala Leu Asp Asp Phe Asp Leu Asp Met Leu Gly Ser Asp Ala Leu
1               5                   10                  15

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Asp Phe Asp Leu Asp
        35                  40                  45

Met Leu
    50

<210> SEQ ID NO 22
<211> LENGTH: 2661
<212> TYPE: DNA
<213> ORGANISM: Artificial Sequence
<220> FEATURE:
<223> OTHER INFORMATION: TALE_TERT-1
<220> FEATURE:

<221> NAME/KEY: CDS
<222> LOCATION: (1)..(2661)

<400> SEQUENCE: 22

| | | | | | | | | | | | | | | | | |
|---|---|---|---|---|---|---|---|---|---|---|---|---|---|---|---|---|
| atc | cac | gga | gtc | cca | gca | gcc | gta | gat | ttg | aga | act | ttg | gga | tat | tca | 48 |
| Ile | His | Gly | Val | Pro | Ala | Ala | Val | Asp | Leu | Arg | Thr | Leu | Gly | Tyr | Ser | |
| 1 | | | | 5 | | | | | 10 | | | | | 15 | | |

| cag | cag | cag | cag | gaa | aag | atc | aag | ccc | aaa | gtg | agg | tcg | aca | gtc | gcg | 96 |
|---|---|---|---|---|---|---|---|---|---|---|---|---|---|---|---|---|
| Gln | Gln | Gln | Gln | Glu | Lys | Ile | Lys | Pro | Lys | Val | Arg | Ser | Thr | Val | Ala | |
| | | | 20 | | | | | 25 | | | | | 30 | | | |

| cag | cat | cac | gaa | gcg | ctg | gtg | ggt | cat | ggg | ttt | aca | cat | gcc | cac | atc | 144 |
|---|---|---|---|---|---|---|---|---|---|---|---|---|---|---|---|---|
| Gln | His | His | Glu | Ala | Leu | Val | Gly | His | Gly | Phe | Thr | His | Ala | His | Ile | |
| | | 35 | | | | | 40 | | | | | 45 | | | | |

| gta | gcc | ttg | tcg | cag | cac | cct | gca | gcc | ctt | ggc | acg | gtc | gcc | gtc | aag | 192 |
|---|---|---|---|---|---|---|---|---|---|---|---|---|---|---|---|---|
| Val | Ala | Leu | Ser | Gln | His | Pro | Ala | Ala | Leu | Gly | Thr | Val | Ala | Val | Lys | |
| 50 | | | | | 55 | | | | | 60 | | | | | | |

| tac | cag | gac | atg | att | gcg | gcg | ttg | ccg | gaa | gcc | aca | cat | gag | gcg | atc | 240 |
|---|---|---|---|---|---|---|---|---|---|---|---|---|---|---|---|---|
| Tyr | Gln | Asp | Met | Ile | Ala | Ala | Leu | Pro | Glu | Ala | Thr | His | Glu | Ala | Ile | |
| 65 | | | | | 70 | | | | | 75 | | | | | 80 | |

| gtc | ggt | gtg | ggg | aaa | cag | tgg | agc | gga | gcc | cga | gcg | ctt | gag | gcc | ctg | 288 |
|---|---|---|---|---|---|---|---|---|---|---|---|---|---|---|---|---|
| Val | Gly | Val | Gly | Lys | Gln | Trp | Ser | Gly | Ala | Arg | Ala | Leu | Glu | Ala | Leu | |
| | | | | 85 | | | | | 90 | | | | | 95 | | |

| ttg | acg | gtc | gcg | gga | gag | ctg | aga | ggg | cct | ccc | ctt | cag | ctg | gac | acg | 336 |
|---|---|---|---|---|---|---|---|---|---|---|---|---|---|---|---|---|
| Leu | Thr | Val | Ala | Gly | Glu | Leu | Arg | Gly | Pro | Pro | Leu | Gln | Leu | Asp | Thr | |
| | | | 100 | | | | | 105 | | | | | 110 | | | |

| ggc | cag | ttg | ctg | aag | atc | gcg | aag | cgg | gga | gga | gtc | acg | gcg | gtc | gag | 384 |
|---|---|---|---|---|---|---|---|---|---|---|---|---|---|---|---|---|
| Gly | Gln | Leu | Leu | Lys | Ile | Ala | Lys | Arg | Gly | Gly | Val | Thr | Ala | Val | Glu | |
| | | | 115 | | | | | 120 | | | | | 125 | | | |

| gcg | gta | cac | gcg | tgg | cgc | aat | gcg | ctc | acg | gga | gca | ccc | ctc | aac | ctg | 432 |
|---|---|---|---|---|---|---|---|---|---|---|---|---|---|---|---|---|
| Ala | Val | His | Ala | Trp | Arg | Asn | Ala | Leu | Thr | Gly | Ala | Pro | Leu | Asn | Leu | |
| 130 | | | | | 135 | | | | | 140 | | | | | | |

| acc | ccg | gac | cag | gtg | gtt | gca | atc | gcg | tca | cac | gat | ggg | gga | aag | cag | 480 |
|---|---|---|---|---|---|---|---|---|---|---|---|---|---|---|---|---|
| Thr | Pro | Asp | Gln | Val | Val | Ala | Ile | Ala | Ser | His | Asp | Gly | Gly | Lys | Gln | |
| 145 | | | | | 150 | | | | | 155 | | | | | 160 | |

| gcc | cta | gaa | acc | gtt | cag | cga | ctc | ctg | ccc | gtc | ctg | tgc | cag | gac | cac | 528 |
|---|---|---|---|---|---|---|---|---|---|---|---|---|---|---|---|---|
| Ala | Leu | Glu | Thr | Val | Gln | Arg | Leu | Leu | Pro | Val | Leu | Cys | Gln | Asp | His | |
| | | | | 165 | | | | | 170 | | | | | 175 | | |

| ggc | ctg | acc | cca | gaa | cag | gtt | gtg | gcc | atc | gcc | agc | aac | ata | ggt | ggc | 576 |
|---|---|---|---|---|---|---|---|---|---|---|---|---|---|---|---|---|
| Gly | Leu | Thr | Pro | Glu | Gln | Val | Val | Ala | Ile | Ala | Ser | Asn | Ile | Gly | Gly | |
| | | | 180 | | | | | 185 | | | | | 190 | | | |

| aag | cag | gcc | ctc | gaa | acc | gtc | cag | aga | ctg | tta | ccg | gtt | ctc | tgc | cag | 624 |
|---|---|---|---|---|---|---|---|---|---|---|---|---|---|---|---|---|
| Lys | Gln | Ala | Leu | Glu | Thr | Val | Gln | Arg | Leu | Leu | Pro | Val | Leu | Cys | Gln | |
| | | | 195 | | | | | 200 | | | | | 205 | | | |

| gcc | cac | ggc | ctg | acc | cca | gac | caa | gtt | gtc | gcg | att | gca | agc | aac | aac | 672 |
|---|---|---|---|---|---|---|---|---|---|---|---|---|---|---|---|---|
| Ala | His | Gly | Leu | Thr | Pro | Asp | Gln | Val | Val | Ala | Ile | Ala | Ser | Asn | Asn | |
| 210 | | | | | 215 | | | | | 220 | | | | | | |

| gga | ggc | aaa | caa | gcc | tta | gaa | aca | gtc | cag | aga | ttg | ttg | cct | gtg | ctg | 720 |
|---|---|---|---|---|---|---|---|---|---|---|---|---|---|---|---|---|
| Gly | Gly | Lys | Gln | Ala | Leu | Glu | Thr | Val | Gln | Arg | Leu | Leu | Pro | Val | Leu | |
| 225 | | | | | 230 | | | | | 235 | | | | | 240 | |

| tgc | caa | gcc | cac | ggc | ctg | acc | cca | gcc | cag | gtt | gtg | gcc | atc | gcc | agc | 768 |
|---|---|---|---|---|---|---|---|---|---|---|---|---|---|---|---|---|
| Cys | Gln | Ala | His | Gly | Leu | Thr | Pro | Ala | Gln | Val | Val | Ala | Ile | Ala | Ser | |
| | | | 245 | | | | | 250 | | | | | 255 | | | |

| aac | ata | ggt | ggc | aag | cag | gcc | ctc | gaa | acc | gtc | cag | aga | ctg | tta | ccg | 816 |
|---|---|---|---|---|---|---|---|---|---|---|---|---|---|---|---|---|
| Asn | Ile | Gly | Gly | Lys | Gln | Ala | Leu | Glu | Thr | Val | Gln | Arg | Leu | Leu | Pro | |
| | | | 260 | | | | | 265 | | | | | 270 | | | |

| gtt | ctc | tgc | cag | gac | cac | ggc | ctg | acc | cca | gac | caa | gtt | gtc | gcg | att | 864 |
|---|---|---|---|---|---|---|---|---|---|---|---|---|---|---|---|---|
| Val | Leu | Cys | Gln | Asp | His | Gly | Leu | Thr | Pro | Asp | Gln | Val | Val | Ala | Ile | |
| | | 275 | | | | | 280 | | | | | 285 | | | | |

| gca | agc | aac | aac | gga | ggc | aaa | caa | gcc | tta | gaa | aca | gtc | cag | aga | ttg | 912 |
|---|---|---|---|---|---|---|---|---|---|---|---|---|---|---|---|---|
| Ala | Ser | Asn | Asn | Gly | Gly | Lys | Gln | Ala | Leu | Glu | Thr | Val | Gln | Arg | Leu | |

|  |  |  |  |  |  |  |  |  |  |  |  |  |  |  |  |
|---|---|---|---|---|---|---|---|---|---|---|---|---|---|---|---|
| | | | | 290 | | | | | 295 | | | | | 300 | |
| ttg | ccg | gtg | ctg | tgc | caa | gac | cac | ggc | ctg | acc | cca | gaa | caa | gtt | gtc | 960
| Leu | Pro | Val | Leu | Cys | Gln | Asp | His | Gly | Leu | Thr | Pro | Glu | Gln | Val | Val |
| 305 | | | | | 310 | | | | | 315 | | | | | 320 |

| gcg | att | gca | agc | aac | aac | gga | ggc | aaa | caa | gcc | tta | gaa | aca | gtc | cag | 1008 |
| Ala | Ile | Ala | Ser | Asn | Asn | Gly | Gly | Lys | Gln | Ala | Leu | Glu | Thr | Val | Gln |
| | | | | 325 | | | | | 330 | | | | | 335 | |

| aga | ttg | ttg | ccg | gtg | ctg | tgc | caa | gcc | cac | ggc | ctg | acc | cca | gac | caa | 1056 |
| Arg | Leu | Leu | Pro | Val | Leu | Cys | Gln | Ala | His | Gly | Leu | Thr | Pro | Asp | Gln |
| | | | 340 | | | | | 345 | | | | | 350 | | |

| gtt | gtc | gcg | att | gca | agc | aac | aac | gga | ggc | aaa | caa | gcc | tta | gaa | aca | 1104 |
| Val | Val | Ala | Ile | Ala | Ser | Asn | Asn | Gly | Gly | Lys | Gln | Ala | Leu | Glu | Thr |
| | | | | 355 | | | | | 360 | | | | | 365 | |

| gtc | cag | aga | ttg | ttg | cct | gtg | ctg | tgc | caa | gcc | cac | ggc | ctg | acc | cca | 1152 |
| Val | Gln | Arg | Leu | Leu | Pro | Val | Leu | Cys | Gln | Ala | His | Gly | Leu | Thr | Pro |
| | | 370 | | | | | 375 | | | | | 380 | | | |

| gcc | cag | gtt | gtg | gcc | atc | gcc | agc | aac | ata | ggt | ggc | aag | cag | gcc | ctc | 1200 |
| Ala | Gln | Val | Val | Ala | Ile | Ala | Ser | Asn | Ile | Gly | Gly | Lys | Gln | Ala | Leu |
| 385 | | | | | 390 | | | | | 395 | | | | | 400 |

| gaa | acc | gtc | cag | aga | ctg | tta | ccg | gtt | ctc | tgc | cag | gac | cac | ggc | ctg | 1248 |
| Glu | Thr | Val | Gln | Arg | Leu | Leu | Pro | Val | Leu | Cys | Gln | Asp | His | Gly | Leu |
| | | | | 405 | | | | | 410 | | | | | 415 | |

| acc | ccg | gac | cag | gtg | gtt | gca | atc | gcg | tca | cac | gat | ggg | gga | aag | cag | 1296 |
| Thr | Pro | Asp | Gln | Val | Val | Ala | Ile | Ala | Ser | His | Asp | Gly | Gly | Lys | Gln |
| | | | 420 | | | | | 425 | | | | | 430 | | |

| gcc | cta | gaa | acc | gtt | cag | cga | ctc | ctg | ccc | gtc | ctg | tgc | cag | gac | cac | 1344 |
| Ala | Leu | Glu | Thr | Val | Gln | Arg | Leu | Leu | Pro | Val | Leu | Cys | Gln | Asp | His |
| | | 435 | | | | | 440 | | | | | 445 | | | |

| ggc | ctg | acc | cca | gaa | caa | gtt | gtc | gcg | att | gca | agc | aac | aac | gga | ggc | 1392 |
| Gly | Leu | Thr | Pro | Glu | Gln | Val | Val | Ala | Ile | Ala | Ser | Asn | Asn | Gly | Gly |
| | 450 | | | | | 455 | | | | | 460 | | | | |

| aaa | caa | gcc | tta | gaa | aca | gtc | cag | aga | ttg | ttg | ccg | gtg | ctg | tgc | caa | 1440 |
| Lys | Gln | Ala | Leu | Glu | Thr | Val | Gln | Arg | Leu | Leu | Pro | Val | Leu | Cys | Gln |
| 465 | | | | | 470 | | | | | 475 | | | | | 480 |

| gcc | cac | ggc | ctg | acc | ccg | gac | cag | gtg | gtt | gca | atc | gcg | tca | cac | gat | 1488 |
| Ala | His | Gly | Leu | Thr | Pro | Asp | Gln | Val | Val | Ala | Ile | Ala | Ser | His | Asp |
| | | | 485 | | | | | 490 | | | | | 495 | | |

| ggg | gga | aag | cag | gcc | cta | gaa | acc | gtt | cag | cga | ctc | ctg | ccc | gtc | ctg | 1536 |
| Gly | Gly | Lys | Gln | Ala | Leu | Glu | Thr | Val | Gln | Arg | Leu | Leu | Pro | Val | Leu |
| | | 500 | | | | | 505 | | | | | 510 | | | |

| tgc | cag | gcc | cac | ggc | ctg | acc | cca | gcc | cag | gtt | gtg | gcc | atc | gcc | agc | 1584 |
| Cys | Gln | Ala | His | Gly | Leu | Thr | Pro | Ala | Gln | Val | Val | Ala | Ile | Ala | Ser |
| | 515 | | | | | 520 | | | | | 525 | | | | |

| aac | ata | ggt | ggc | aag | cag | gcc | ctc | gaa | acc | gtc | cag | aga | ctg | tta | ccg | 1632 |
| Asn | Ile | Gly | Gly | Lys | Gln | Ala | Leu | Glu | Thr | Val | Gln | Arg | Leu | Leu | Pro |
| 530 | | | | | 535 | | | | | 540 | | | | | |

| gtt | ctc | tgc | cag | gac | cac | ggc | ctg | acc | cca | gac | caa | gtt | gtc | gcg | att | 1680 |
| Val | Leu | Cys | Gln | Asp | His | Gly | Leu | Thr | Pro | Asp | Gln | Val | Val | Ala | Ile |
| 545 | | | | | 550 | | | | | 555 | | | | | 560 |

| gca | agc | aac | aac | gga | ggc | aaa | caa | gcc | tta | gaa | aca | gtc | cag | aga | ttg | 1728 |
| Ala | Ser | Asn | Asn | Gly | Gly | Lys | Gln | Ala | Leu | Glu | Thr | Val | Gln | Arg | Leu |
| | | | | 565 | | | | | 570 | | | | | 575 | |

| ttg | ccg | gtg | ctg | tgc | caa | gac | cac | ggc | ctg | acc | ccc | gaa | cag | gtt | gtc | 1776 |
| Leu | Pro | Val | Leu | Cys | Gln | Asp | His | Gly | Leu | Thr | Pro | Glu | Gln | Val | Val |
| | | | 580 | | | | | 585 | | | | | 590 | | |

| gct | att | gct | agt | aac | ggc | gga | ggc | aaa | cag | gcg | ctg | gaa | aca | gtt | cag | 1824 |
| Ala | Ile | Ala | Ser | Asn | Gly | Gly | Gly | Lys | Gln | Ala | Leu | Glu | Thr | Val | Gln |
| | | | | 595 | | | | | 600 | | | | | 605 | |

| cgc | ctc | ttg | ccg | gtc | ttg | tgt | cag | gcc | cac | ggc | ctg | acc | ccg | gac | cag | 1872 |

```
Arg Leu Leu Pro Val Leu Cys Gln Ala His Gly Leu Thr Pro Asp Gln
        610             615                 620 gtg gtt gca atc gcg tca cac gat ggg gga aag cag gcc cta gaa acc      1920
Val Val Ala Ile Ala Ser His Asp Gly Gly Lys Gln Ala Leu Glu Thr
625             630                 635                 640 gtt cag cga ctc ctg ccc gtc ctg tgc cag gcc cac ggc ctg acc ccc      1968
Val Gln Arg Leu Leu Pro Val Leu Cys Gln Ala His Gly Leu Thr Pro
            645                 650                 655 gcc cag gtt gtc gct att gct agt aac ggc gga ggc aaa cag gcg ctg      2016
Ala Gln Val Val Ala Ile Ala Ser Asn Gly Gly Gly Lys Gln Ala Leu
        660                 665                 670 gaa aca gtt cag cgc ctc ttg ccg gtc ttg tgt cag gac cac ggc ctg      2064
Glu Thr Val Gln Arg Leu Leu Pro Val Leu Cys Gln Asp His Gly Leu
    675                 680                 685 acc cct gag cag gta gtg gct att gca tcc cac gac ggg ggc aga ccc      2112
Thr Pro Glu Gln Val Val Ala Ile Ala Ser His Asp Gly Gly Arg Pro
690                 695                 700 gca ctg gag tca atc gtg gcc cag ctc tcg agg ccg gac ccc gcg ctg      2160
Ala Leu Glu Ser Ile Val Ala Gln Leu Ser Arg Pro Asp Pro Ala Leu
705                 710                 715                 720 gcc gca ctc act aat gat cat ctt gta gcg ctg gcc tgc ctc ggc gga      2208
Ala Ala Leu Thr Asn Asp His Leu Val Ala Leu Ala Cys Leu Gly Gly
                725                 730                 735 cga ccc gcc ttg gat gcg gtg aag aag ggg ctc ccg cac gcg cct gca      2256
Arg Pro Ala Leu Asp Ala Val Lys Lys Gly Leu Pro His Ala Pro Ala
            740                 745                 750 ttg att aag cgg acc aac aga agg atc ccc gag agg aca tca cat cga      2304
Leu Ile Lys Arg Thr Asn Arg Arg Ile Pro Glu Arg Thr Ser His Arg
        755                 760                 765 gtg gca gat cac gcg caa gtg gtc cgc gtg ctc gga ttc ttc cag tgt      2352
Val Ala Asp His Ala Gln Val Val Arg Val Leu Gly Phe Phe Gln Cys
770                 775                 780 cac tcc cac ccc gca caa gcg ttc gat gac gcc atg act caa ttt ggt      2400
His Ser His Pro Ala Gln Ala Phe Asp Asp Ala Met Thr Gln Phe Gly
785                 790                 795                 800 atg tcg aga cac gga ctg ctg cag ctc ttt cgt aga gtc ggt gtc aca      2448
Met Ser Arg His Gly Leu Leu Gln Leu Phe Arg Arg Val Gly Val Thr
                805                 810                 815 gaa ctg gag gcc cgc tcg ggc aca ctg cct ccc gcc tcc cag cgg tgg      2496
Glu Leu Glu Ala Arg Ser Gly Thr Leu Pro Pro Ala Ser Gln Arg Trp
            820                 825                 830 gac agg att ctc caa gcg agc ggt atg aaa cgc gcg aag cct tca cct      2544
Asp Arg Ile Leu Gln Ala Ser Gly Met Lys Arg Ala Lys Pro Ser Pro
        835                 840                 845 acg tca act cag aca cct gac cag gcg agc ctt cat gcg ttc gca gac      2592
Thr Ser Thr Gln Thr Pro Asp Gln Ala Ser Leu His Ala Phe Ala Asp
850                 855                 860 tcg ctg gag agg gat ttg gac gcg ccc tcg ccc atg cat gaa ggg gac      2640
Ser Leu Glu Arg Asp Leu Asp Ala Pro Ser Pro Met His Glu Gly Asp
865                 870                 875                 880 caa act cgc gcg tca gcc agc                                          2661
Gln Thr Arg Ala Ser Ala Ser
                885

<210> SEQ ID NO 23
<211> LENGTH: 887
<212> TYPE: PRT
<213> ORGANISM: Artificial Sequence
<220> FEATURE:
<223> OTHER INFORMATION: Synthetic Construct
```

<400> SEQUENCE: 23

```
Ile His Gly Val Pro Ala Ala Val Asp Leu Arg Thr Leu Gly Tyr Ser
1               5                   10                  15
Gln Gln Gln Gln Glu Lys Ile Lys Pro Lys Val Arg Ser Thr Val Ala
            20                  25                  30
Gln His His Glu Ala Leu Val Gly His Gly Phe Thr His Ala His Ile
        35                  40                  45
Val Ala Leu Ser Gln His Pro Ala Ala Leu Gly Thr Val Ala Val Lys
    50                  55                  60
Tyr Gln Asp Met Ile Ala Ala Leu Pro Glu Ala Thr His Glu Ala Ile
65                  70                  75                  80
Val Gly Val Gly Lys Gln Trp Ser Gly Ala Arg Ala Leu Glu Ala Leu
                85                  90                  95
Leu Thr Val Ala Gly Glu Leu Arg Gly Pro Leu Gln Leu Asp Thr
            100                 105                 110
Gly Gln Leu Leu Lys Ile Ala Lys Arg Gly Gly Val Thr Ala Val Glu
        115                 120                 125
Ala Val His Ala Trp Arg Asn Ala Leu Thr Gly Ala Pro Leu Asn Leu
    130                 135                 140
Thr Pro Asp Gln Val Val Ala Ile Ala Ser His Asp Gly Gly Lys Gln
145                 150                 155                 160
Ala Leu Glu Thr Val Gln Arg Leu Leu Pro Val Leu Cys Gln Asp His
                165                 170                 175
Gly Leu Thr Pro Glu Gln Val Val Ala Ile Ala Ser Asn Ile Gly Gly
            180                 185                 190
Lys Gln Ala Leu Glu Thr Val Gln Arg Leu Leu Pro Val Leu Cys Gln
        195                 200                 205
Ala His Gly Leu Thr Pro Asp Gln Val Val Ala Ile Ala Ser Asn Asn
    210                 215                 220
Gly Gly Lys Gln Ala Leu Glu Thr Val Gln Arg Leu Leu Pro Val Leu
225                 230                 235                 240
Cys Gln Ala His Gly Leu Thr Pro Ala Gln Val Val Ala Ile Ala Ser
                245                 250                 255
Asn Ile Gly Gly Lys Gln Ala Leu Glu Thr Val Gln Arg Leu Leu Pro
            260                 265                 270
Val Leu Cys Gln Asp His Gly Leu Thr Pro Asp Gln Val Val Ala Ile
        275                 280                 285
Ala Ser Asn Asn Gly Gly Lys Gln Ala Leu Glu Thr Val Gln Arg Leu
    290                 295                 300
Leu Pro Val Leu Cys Gln Asp His Gly Leu Thr Pro Glu Gln Val Val
305                 310                 315                 320
Ala Ile Ala Ser Asn Asn Gly Gly Lys Gln Ala Leu Glu Thr Val Gln
                325                 330                 335
Arg Leu Leu Pro Val Leu Cys Gln Ala His Gly Leu Thr Pro Asp Gln
            340                 345                 350
Val Val Ala Ile Ala Ser Asn Asn Gly Gly Lys Gln Ala Leu Glu Thr
        355                 360                 365
Val Gln Arg Leu Leu Pro Val Leu Cys Gln Ala His Gly Leu Thr Pro
    370                 375                 380
Ala Gln Val Val Ala Ile Ala Ser Asn Ile Gly Gly Lys Gln Ala Leu
385                 390                 395                 400
Glu Thr Val Gln Arg Leu Leu Pro Val Leu Cys Gln Asp His Gly Leu
                405                 410                 415
```

```
Thr Pro Asp Gln Val Val Ala Ile Ala Ser His Asp Gly Lys Gln
            420                 425                 430

Ala Leu Glu Thr Val Gln Arg Leu Leu Pro Val Leu Cys Gln Asp His
            435                 440                 445

Gly Leu Thr Pro Glu Gln Val Val Ala Ile Ala Ser Asn Asn Gly Gly
            450                 455                 460

Lys Gln Ala Leu Glu Thr Val Gln Arg Leu Leu Pro Val Leu Cys Gln
465                 470                 475                 480

Ala His Gly Leu Thr Pro Asp Gln Val Val Ala Ile Ala Ser His Asp
                    485                 490                 495

Gly Gly Lys Gln Ala Leu Glu Thr Val Gln Arg Leu Leu Pro Val Leu
                500                 505                 510

Cys Gln Ala His Gly Leu Thr Pro Ala Gln Val Val Ala Ile Ala Ser
            515                 520                 525

Asn Ile Gly Gly Lys Gln Ala Leu Glu Thr Val Gln Arg Leu Leu Pro
530                 535                 540

Val Leu Cys Gln Asp His Gly Leu Thr Pro Asp Gln Val Val Ala Ile
545                 550                 555                 560

Ala Ser Asn Asn Gly Gly Lys Gln Ala Leu Glu Thr Val Gln Arg Leu
                565                 570                 575

Leu Pro Val Leu Cys Gln Asp His Gly Leu Thr Pro Glu Gln Val Val
            580                 585                 590

Ala Ile Ala Ser Asn Gly Gly Gly Lys Gln Ala Leu Glu Thr Val Gln
            595                 600                 605

Arg Leu Leu Pro Val Leu Cys Gln Ala His Gly Leu Thr Pro Asp Gln
        610                 615                 620

Val Val Ala Ile Ala Ser His Asp Gly Gly Lys Gln Ala Leu Glu Thr
625                 630                 635                 640

Val Gln Arg Leu Leu Pro Val Leu Cys Gln Ala His Gly Leu Thr Pro
                645                 650                 655

Ala Gln Val Val Ala Ile Ala Ser Asn Gly Gly Gly Lys Gln Ala Leu
            660                 665                 670

Glu Thr Val Gln Arg Leu Leu Pro Val Leu Cys Gln Asp His Gly Leu
            675                 680                 685

Thr Pro Glu Gln Val Val Ala Ile Ala Ser His Asp Gly Gly Arg Pro
        690                 695                 700

Ala Leu Glu Ser Ile Val Ala Gln Leu Ser Arg Pro Asp Pro Ala Leu
705                 710                 715                 720

Ala Ala Leu Thr Asn Asp His Leu Val Ala Leu Ala Cys Leu Gly Gly
                725                 730                 735

Arg Pro Ala Leu Asp Ala Val Lys Lys Gly Leu Pro His Ala Pro Ala
            740                 745                 750

Leu Ile Lys Arg Thr Asn Arg Arg Ile Pro Glu Arg Thr Ser His Arg
            755                 760                 765

Val Ala Asp His Ala Gln Val Val Arg Val Leu Gly Phe Phe Gln Cys
        770                 775                 780

His Ser His Pro Ala Gln Ala Phe Asp Asp Ala Met Thr Gln Phe Gly
785                 790                 795                 800

Met Ser Arg His Gly Leu Leu Gln Leu Phe Arg Arg Val Gly Val Thr
                805                 810                 815

Glu Leu Glu Ala Arg Ser Gly Thr Leu Pro Pro Ala Ser Gln Arg Trp
            820                 825                 830
```

```
Asp Arg Ile Leu Gln Ala Ser Gly Met Lys Arg Ala Lys Pro Ser Pro
            835                 840                 845

Thr Ser Thr Gln Thr Pro Asp Gln Ala Ser Leu His Ala Phe Ala Asp
        850                 855                 860

Ser Leu Glu Arg Asp Leu Asp Ala Pro Ser Pro Met His Glu Gly Asp
865                 870                 875                 880

Gln Thr Arg Ala Ser Ala Ser
                885

<210> SEQ ID NO 24
<211> LENGTH: 38
<212> TYPE: DNA
<213> ORGANISM: Artificial Sequence
<220> FEATURE:
<223> OTHER INFORMATION: Primer

<400> SEQUENCE: 24
cccgcgatcg caccatgatc cacggagtcc cagcagcc                           38

<210> SEQ ID NO 25
<211> LENGTH: 35
<212> TYPE: DNA
<213> ORGANISM: Artificial Sequence
<220> FEATURE:
<223> OTHER INFORMATION: Primer

<400> SEQUENCE: 25
gatttcgacc tggacatgct gtaagcggcc gcggg                              35

<210> SEQ ID NO 26
<211> LENGTH: 36
<212> TYPE: DNA
<213> ORGANISM: Artificial Sequence
<220> FEATURE:
<223> OTHER INFORMATION: Primer

<400> SEQUENCE: 26
cgcgcgtcag ccagcgacgc attggacgat tttgat                             36

<210> SEQ ID NO 27
<211> LENGTH: 36
<212> TYPE: DNA
<213> ORGANISM: Artificial Sequence
<220> FEATURE:
<223> OTHER INFORMATION: Primer

<400> SEQUENCE: 27
ggccgcagtt taaacaaaca gagatgtgtc gaagat                             36

<210> SEQ ID NO 28
<211> LENGTH: 520
<212> TYPE: PRT
<213> ORGANISM: Artificial Sequence
<220> FEATURE:
<223> OTHER INFORMATION: VPR

<400> SEQUENCE: 28

Asp Ala Leu Asp Asp Phe Asp Leu Asp Met Leu Gly Ser Asp Ala Leu
1               5                   10                  15

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Asp Phe Asp Leu Asp
        35                  40                  45
```

-continued

```
Met Leu Ser Ser Gly Ser Pro Lys Lys Arg Lys Val Gly Ser Gln
    50                  55                  60

Tyr Leu Pro Asp Thr Asp Arg His Arg Ile Glu Glu Lys Arg Lys
65                  70                  75                  80

Arg Thr Tyr Glu Thr Phe Lys Ser Ile Met Lys Lys Ser Pro Phe Ser
                        85                  90                  95

Gly Pro Thr Asp Pro Arg Pro Pro Arg Arg Ile Ala Val Pro Ser
                100                 105                 110

Arg Ser Ser Ala Ser Val Pro Lys Pro Ala Pro Gln Pro Tyr Pro Phe
                115                 120                 125

Thr Ser Ser Leu Ser Thr Ile Asn Tyr Asp Glu Phe Pro Thr Met Val
        130                 135                 140

Phe Pro Ser Gly Gln Ile Ser Gln Ala Ser Ala Leu Ala Pro Ala Pro
145                 150                 155                 160

Pro Gln Val Leu Pro Gln Ala Pro Ala Pro Ala Pro Ala Pro Ala Met
                165                 170                 175

Val Ser Ala Leu Ala Gln Ala Pro Ala Pro Val Pro Val Leu Ala Pro
                180                 185                 190

Gly Pro Pro Gln Ala Val Ala Pro Pro Ala Pro Lys Pro Thr Gln Ala
                195                 200                 205

Gly Glu Gly Thr Leu Ser Glu Ala Leu Leu Gln Leu Gln Phe Asp Asp
        210                 215                 220

Glu Asp Leu Gly Ala Leu Leu Gly Asn Ser Thr Asp Pro Ala Val Phe
225                 230                 235                 240

Thr Asp Leu Ala Ser Val Asp Asn Ser Glu Phe Gln Gln Leu Leu Asn
                245                 250                 255

Gln Gly Ile Pro Val Ala Pro His Thr Thr Glu Pro Met Leu Met Glu
                260                 265                 270

Tyr Pro Glu Ala Ile Thr Arg Leu Val Thr Gly Ala Gln Arg Pro Pro
                275                 280                 285

Asp Pro Ala Pro Ala Pro Leu Gly Ala Pro Gly Leu Pro Asn Gly Leu
                290                 295                 300

Leu Ser Gly Asp Glu Asp Phe Ser Ser Ile Ala Asp Met Asp Phe Ser
305                 310                 315                 320

Ala Leu Leu Gly Ser Gly Ser Gly Ser Arg Asp Ser Arg Glu Gly Met
                325                 330                 335

Phe Leu Pro Lys Pro Glu Ala Gly Ser Ala Ile Ser Asp Val Phe Glu
                340                 345                 350

Gly Arg Glu Val Cys Gln Pro Lys Arg Ile Arg Pro Phe His Pro Pro
                355                 360                 365

Gly Ser Pro Trp Ala Asn Arg Pro Leu Pro Ala Ser Leu Ala Pro Thr
                370                 375                 380

Pro Thr Gly Pro Val His Glu Pro Val Gly Ser Leu Thr Pro Ala Pro
385                 390                 395                 400

Val Pro Gln Pro Leu Asp Pro Ala Pro Ala Val Thr Pro Glu Ala Ser
                        405                 410                 415

His Leu Leu Glu Asp Pro Asp Glu Glu Thr Ser Gln Ala Val Lys Ala
                        420                 425                 430

Leu Arg Glu Met Ala Asp Thr Val Ile Pro Gln Lys Glu Glu Ala Ala
                        435                 440                 445

Ile Cys Gly Gln Met Asp Leu Ser His Pro Pro Pro Arg Gly His Leu
450                 455                 460

Asp Glu Leu Thr Thr Thr Leu Glu Ser Met Thr Glu Asp Leu Asn Leu
```

```
            465                 470                 475                 480
Asp Ser Pro Leu Thr Pro Glu Leu Asn Glu Ile Leu Asp Thr Phe Leu
                485                 490                 495

Asn Asp Glu Cys Leu Leu His Ala Met His Ile Ser Thr Gly Leu Ser
            500                 505                 510

Ile Phe Asp Thr Ser Leu Phe Val
            515                 520

<210> SEQ ID NO 29
<211> LENGTH: 15
<212> TYPE: DNA
<213> ORGANISM: Artificial Sequence
<220> FEATURE:
<223> OTHER INFORMATION: VPR-PCR 5'-terminal

<400> SEQUENCE: 29
cgcgcgtcag ccagc                                                         15

<210> SEQ ID NO 30
<211> LENGTH: 15
<212> TYPE: DNA
<213> ORGANISM: Artificial Sequence
<220> FEATURE:
<223> OTHER INFORMATION: VPR-PCR 3'-terminal

<400> SEQUENCE: 30
gtttaaactg cggcc                                                         15

<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31
gtttaaactg cggccgcgtc g                                                  21

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32
gctggctgac gcgcgagttt g                                                  21

<210> SEQ ID NO 33
<211> LENGTH: 341
<212> TYPE: DNA
<213> ORGANISM: Artificial Sequence
<220> FEATURE:
<223> OTHER INFORMATION: NTP(ICQ2)

<400> SEQUENCE: 33
acatatttaa atggtgatca tgtaacccat cctgacttca tgttgtatga cgctcttgat        60
gttgttttat acatggaccc aatgtgcctg gatgcgttcc caaaattagt ttgttttaaa       120
aaacgtattg aagctatccc acaaattgat aagtacttga atccagcaa gtatatagca        180 tggcctttgc agggctggca agccacgttt ggtggtggcg accatcctcc aaaatcggat       240
ctggaagttc tgttccaggg gccctggga tccaggatct tcatccactt ccggcagggc        300
```
caggaaaacc tgtatttcca atctctcgag cgcgatcgca c                              341

<210> SEQ ID NO 34
<211> LENGTH: 341
<212> TYPE: DNA
<213> ORGANISM: Artificial Sequence
<220> FEATURE:
<223> OTHER INFORMATION: NTP(I8Q)

<400> SEQUENCE: 34
acatatttaa atggtgatca tgtaacccat cctgacttca tgttgtatga cgctcttgat         60
gttgttttat acatggaccc aatgtgcctg gatgcgttcc caaaattagt ttgttttaaa       120
aaacgtattg aagctatccc acaaattgat aagtacttga atccagcaa gtatatagca        180
tggcctttgc agggctggca agccacgttt ggtggtggcg accatcctcc aaaatcggat      240
ctggaagttc tgttccaggg gcccctggga tccaggatct tcatccactt ccggcagggc      300
tgcgaaaacc tgtatttcca atctctcgag cgcgatcgca c                              341

<210> SEQ ID NO 35
<211> LENGTH: 341
<212> TYPE: DNA
<213> ORGANISM: Artificial Sequence
<220> FEATURE:
<223> OTHER INFORMATION: NTP(C10Q)

<400> SEQUENCE: 35
acatatttaa atggtgatca tgtaacccat cctgacttca tgttgtatga cgctcttgat         60
gttgttttat acatggaccc aatgtgcctg gatgcgttcc caaaattagt ttgttttaaa       120
aaacgtattg aagctatccc acaaattgat aagtacttga atccagcaa gtatatagca        180
tggcctttgc agggctggca agccacgttt ggtggtggcg accatcctcc aaaatcggat      240
ctggaagttc tgttccaggg gcccctggga tccaggatct tcatccactt ccggatcggc      300
caggaaaacc tgtatttcca atctctcgag cgcgatcgca c                              341

<210> SEQ ID NO 36
<211> LENGTH: 25
<212> TYPE: DNA
<213> ORGANISM: Artificial Sequence
<220> FEATURE:
<223> OTHER INFORMATION: Primer

<400> SEQUENCE: 36
gaaaacctgt atttccaatc tctcg                                                25

<210> SEQ ID NO 37
<211> LENGTH: 36
<212> TYPE: DNA
<213> ORGANISM: Artificial Sequence
<220> FEATURE:
<223> OTHER INFORMATION: Primer

<400> SEQUENCE: 37
gaaatacagg ttttcatccg attttggagg atggtc                                    36

<210> SEQ ID NO 38
<211> LENGTH: 21
<212> TYPE: DNA
<213> ORGANISM: Artificial Sequence
<220> FEATURE:
<223> OTHER INFORMATION: Primer

<400> SEQUENCE: 38

```
ggagcaagtt gcaaagcatt g                                              21

<210> SEQ ID NO 39
<211> LENGTH: 21
<212> TYPE: DNA
<213> ORGANISM: Artificial Sequence
<220> FEATURE:
<223> OTHER INFORMATION: Primer

<400> SEQUENCE: 39
tgggagcagc tactggatct t                                              21

<210> SEQ ID NO 40
<211> LENGTH: 19
<212> TYPE: DNA
<213> ORGANISM: Artificial Sequence
<220> FEATURE:
<223> OTHER INFORMATION: Primer

<400> SEQUENCE: 40
gatcggcggc tccatcctg                                                 19

<210> SEQ ID NO 41
<211> LENGTH: 22
<212> TYPE: DNA
<213> ORGANISM: Artificial Sequence
<220> FEATURE:
<223> OTHER INFORMATION: Primer

<400> SEQUENCE: 41
gactcgtcat actcctgctt gc                                             22
```

CELL PENETRATING PEPTIDE

CROSS-REFERENCE TO RELATED APPLICATIONS

This application is a Divisional of U.S. application Ser. No. 16/771,009, which is the U.S. National Stage of PCT/JP2018/045228, filed Dec. 10, 2018, which claims priority to JP 2017-236660, filed Dec. 11, 2017.

The instant application contains a Sequence Listing which has been submitted in ASCII format via EFS-WEB and is hereby incorporated by reference in its entirety. Said ASCII copy, created on Jun. 29, 2022, is named sequence.txt and is 44,659 bytes.

TECHNICAL FIELD

The present invention relates to a cell penetrating peptide.

BACKGROUND ART

A cell penetrating peptide is a peptide having an ability to pass through cell membrane and migrate into the inside of cells. As the cell penetrating peptide, various sequences such as TAT derived from a human immunodeficiency virus (HIV), Penetratin, Oligoarginine, Transportan and a membrane transduction sequence are known (Pharmacol. Ther., 2015, Vol. 154, p. 78-86). Also, a cell penetrating peptide, RIFIHFRIGC (SEQ ID NO: 4), which was found from a sequence of a peptide comprised in HIV-1 Viral Protein R protein, is reported (Patent Literature 1).

CITATION LIST

Patent Literature

[Patent Literature 1] International Publication No. WO 2008/108505

SUMMARY OF INVENTION

Technical Problem

An object of the present invention is to provide novel cell penetrating peptides having a penetrating ability into a cell.

Solution to Problem

The present inventors conducted intensive studies with a view to prepare a cell penetrating peptide. As a result, they prepared novel cell penetrating peptides (Examples 1 and 2) and found that these peptides have a penetrating ability into a cell (Examples 3 and 4). Consequently, the cell penetrating peptides were provided and the present invention was accomplished.

More specifically, the present invention may comprise the following inventions as a medically or industrially useful substance or method.

[1] A peptide selected from the group consisting of (1) to (3):
(1) a peptide consisting of an amino acid sequence of SEQ ID NO: 1;
(2) a peptide consisting of an amino acid sequence of SEQ ID NO: 2; and
(3) a peptide consisting of an amino acid sequence of SEQ ID NO: 3.
[2] The peptide according to [1], consisting of the amino acid sequence of SEQ ID NO: 1.
[3] The peptide according to [1], consisting of the amino acid sequence of SEQ ID NO: 2.
[4] The peptide according to [1], consisting of the amino acid sequence of SEQ ID NO: 3.
[5] A complex comprising the peptide according to [1] and a functional molecule.
[6] A polynucleotide comprising a nucleotide sequence encoding the peptide according to [1].
[7] A polynucleotide comprising a nucleotide sequence encoding the complex according to [5].

Advantageous Effects of Invention

The cell penetrating peptide of the present invention can be used for penetration of an arbitrary peptide into a cell.

BRIEF DESCRIPTION OF DRAWINGS

FIG. 1 The figure shows the ability of CPP-EGFP protein to be uptaken by cells. The vertical axis represents the ratio of cells emitting EGFP relative to the total cells. The control is a group of cells to which only a solvent was added. The error bars each indicate a standard deviation of measurement values of overlapped triple test samples.

FIG. 2 The figure shows comparative effects of CPP-TALE-Activators to increase human TERT mRNA expression. The vertical axis represents the relative human TERT mRNA expression levels of each test sample to the relative expression level of human TERT mRNA of the control regarded as 1. The error bars each indicate a standard deviation of measurement values of overlapped three test samples.

FIG. 3 The figure shows comparative effects of NTP-TALE-VPR and TALE-VPR to increase human TERT mRNA expression. The vertical axis represents the relative human TERT mRNA expression levels of each test sample to the relative expression level of human TERT mRNA of the control regarded as 1. The error bars each indicate a standard deviation of measurement values of overlapped triple test samples.

FIG. 4A The figure shows the analysis results of Green Fluorescent Protein Fluorescence-Detection Size-Exclusion Chromatography (GFP-FSEC). The vertical axis of the graph represents the amount of GFP fusion protein measured based on fluorescence intensity; whereas the horizontal axis represents the excluded volume of buffer. Graph (1) shows the results of NTP-GST-EGFP; graph (2) shows the results of NTP (C10Q)-GST-EGFP, graph (3) shows the results of NTP (I8Q)-GST-EGFP and graph (4) shows the results of NTP (ICQ2)-GST-EGFP.

FIG. 4B The figure shows the results of the four samples shown in FIG. 4A mutually superimposed.

DESCRIPTION OF EMBODIMENTS

The present invention will be more specifically described below. The following embodiments are just examples for illustrating the present invention and should not be construed as limiting the present invention only to the embodiments. The present invention can be carried out in various ways within the scope of the invention. The specification incorporates the contents of the specification and drawings of Japanese Patent Application No. 2017-236660 filed on Dec. 11, 2017, based on which the priority right of the present application is claimed.

1. Cell Penetrating Peptide of the Present Invention

The cell penetrating peptide of the present invention is a peptide selected from the group consisting of (1) to (3):
(1) a peptide consisting of an amino acid sequence of SEQ ID NO: 1;
(2) a peptide consisting of an amino acid sequence of SEQ ID NO: 2; and
(3) a peptide consisting of an amino acid sequence of SEQ ID NO: 3.

The "cell penetrating peptide" in the specification refers to a peptide having an ability to pass through cell membrane. Whether a peptide passes through cell membrane or not can be checked by use of a cell-membrane penetration evaluation system known in the art. Examples of the evaluation system include a labeled protein intracellular detection system using a complex comprising an enhanced sensitive green fluorescent protein (EGFP) and a test peptide; and a gene expression evaluation system using a complex comprising a deoxyribonucleic acid (DNA) binding polypeptide, a transcriptional regulator and a test peptide. If a complex comprising an EGFP and a test peptide is used, penetration ability of a test peptide through cell membrane can be evaluated, for example, based on emission from EGFP taken in cells as an index. If the gene expression evaluation system using a complex comprising a DNA binding polypeptide, a transcriptional regulator and a test peptide is used, penetrating ability of a test peptide through cell membrane can be evaluated based on the target-gene expression level as an index. As an evaluation method, for example, methods described in Examples 3 and 4 can be used.

2. Complex of the Present Invention

The complex of the present invention is a complex comprising a cell penetrating peptide of the present invention and a functional molecule.

There is a wide variety of functional molecules that can be used in combination with the cell penetrating peptide of the present invention. The functional molecule to be comprised in the complex of the present invention is not particularly limited as long as it shows its functions. Examples thereof include low molecular compounds, polynucleotides, polypeptides, lipids, carbohydrates, other high molecular compounds, magnetic particles and physiologically active substances such as liposomes.

As the polynucleotide to be comprised in the complex of the present invention, DNA or a ribonucleic acid (RNA including aptamers) of any length can be used. The DNA or ribonucleic acid to be used may be naturally occurring one or a synthesized one. The polynucleotide may be a single strand or a double strand. A plurality of polynucleotides can be used.

If the polynucleotide is DNA, DNA encoding a physiologically active polypeptide can be used. Examples of the physiologically active polypeptide include hormones, growth factors, enzymes, cytokines, antigen peptides for vaccines, receptors, antibodies, transcription factors, structural proteins and fusion polypeptides.

If the polynucleotide is RNA, examples of RNA include small nuclear RNA (snRNA), small nucleolar RNA (snoRNA), small temporal RNA (stRNA), small interfering RNA (siRNA), microRNA (miRNA), precursor miRNA (pre-miRNA), small hairpin RNA (shRNA), viral RNA, antisense RNA and messenger RNA (mRNA).

Examples of the polypeptide to be comprised in the complex of the present invention include hormones, growth factors, enzymes, cytokines, antigen peptides for vaccines, receptors, antibodies, transcription factors, structural proteins and fusion polypeptides.

In an embodiment, examples of the fusion polypeptide to be comprised in the complex of the present invention include fusion polypeptides to be used as genome editing technology (Proc. Natl. Acad. Sci. USA., 1996, Vol. 93, p. 1156-1160; Genetics, 2010, Vol. 186, p. 757-761; Science, 2013, Vol. 339, p. 819-823; Science, 2013, Vol. 339, p. 823-826; Methods Mol. Biol., 2016, Vol. 1469, p. 147-155; Nat. Methods, 2013, Vol. 10, p. 977-979). In another embodiment, the complex of the present invention may include a polynucleotide encoding the fusion polypeptide.

The cell penetrating peptide and functional molecule to be comprised in the complex of the present invention may be directly bound or indirectly bound with each other via a linker.

The linker to be used for binding a cell penetrating peptide and a functional molecule is not limited as long as the resultant complex passes through cell membrane and shows functions of the functional molecule.

The size of the complex of the present invention (e.g., diameter and length), which is not limited as long as the complex passes through cell membrane, falls within the range of, e.g., about 0.1 to 500 nm. Although the length of the functional molecule to be comprised in the complex of the present invention is not limited; for example, if the functional molecule is RNA, the length is about 5000 nucleotides or less; if the functional molecule is DNA, the length is about 20,000 base pairs (hereinafter referred to simply as bp) or less; and if the functional molecule is a polypeptide, the length is about 3000 amino acids or less.

3. Polynucleotide of the Present Invention

Examples of the polynucleotide of the present invention include a polynucleotide comprising the nucleotide sequence encoding a cell penetrating peptide of the present invention and a polynucleotide comprising the nucleotide sequence encoding a complex of the present invention.

In an embodiment, the polynucleotide of the present invention is a polynucleotide selected from the group consisting of the following (1) to (3):
(1) a polynucleotide comprising a nucleotide sequence encoding a peptide consisting of the amino acid sequence of SEQ ID NO: 1;
(2) a polynucleotide comprising a nucleotide sequence encoding a peptide consisting of the amino acid sequence of SEQ ID NO: 2; and
(3) a polynucleotide comprising a nucleotide sequence encoding a peptide consisting of the amino acid sequence of SEQ ID NO: 3.

In an embodiment, the polynucleotide of the present invention is a polynucleotide selected from the group consisting of the following (1) to (3):
(1) a polynucleotide comprising a nucleotide sequence from nucleotide positions 274 to 303 in SEQ ID NO: 33;
(2) a polynucleotide comprising a nucleotide sequence from nucleotide positions 274 to 303 in SEQ ID NO: 34; and
(3) a polynucleotide comprising a nucleotide sequence from nucleotide positions 274 to 303 in SEQ ID NO: 35.

The polynucleotide of the present invention can be synthesized based on the nucleotide sequence designed in accordance with the amino acid sequence of the cell penetrating peptide of the present invention or the complex of the present invention, by using a gene synthesis method known in the technical field (for example, J. Biol. Chem., 1982, Vol. 257, p. 9226-9229).

4. Expression Vector of the Present Invention

Examples of the expression vector of the present invention include an expression vector comprising a polynucleotide comprising the nucleotide sequence encoding the cell penetrating peptide of the present invention and an expression vector comprising a polynucleotide comprising a nucleotide sequence encoding the complex of the present invention.

In an embodiment, the expression vector of the present invention is an expression vector comprising a polynucleotide of the present invention selected from the group consisting of the following (1) to (3):
(1) an expression vector comprising a polynucleotide comprising a nucleotide sequence encoding a peptide consisting of the amino acid sequence of SEQ ID NO: 1;
(2) an expression vector comprising a polynucleotide comprising a nucleotide sequence encoding a peptide consisting of the amino acid sequence of SEQ ID NO: 2; and
(3) an expression vector comprising a polynucleotide comprising a nucleotide sequence encoding a peptide consisting of the amino acid sequence of SEQ ID NO: 3.

As the expression vector to be used for expressing a polynucleotide of the present invention is not limited as long as it expresses a polynucleotide comprising a nucleotide sequence encoding a cell penetrating peptide or complex of the present invention in various host cells such as eukaryotic cells (for example, animal cells, insect cells, plant cells, yeasts) and/or prokaryotic cells (for example, *Escherichia*), or in a cell extract used for cell-free protein synthesis (hereinafter referred to as a cell-free protein synthesis solution, including a wheat germ extract, an *E. coli* extract, a rabbit reticulocyte extract and an insect cell extract) to produce a polypeptide encoded by the nucleotide sequence. Examples of the expression vector include plasmid vectors and viral vectors (for example, adenovirus, adeno-associated virus, retro virus, Sendai virus vectors). Preferably, pEU-E01-MCS (CellFree Sciences), pET20b (+) (Novagen) and pCold vector-I (Takara Bio Inc.) can be used.

The expression vector of the present invention may comprise a promotor functionally ligated to the polynucleotide of the present invention. Examples of the promoter for use in expressing the polynucleotide of the present invention in animal cells include promoters derived from viruses such as Cytomegalovirus (CMV), Respiratory syncytial virus (RSV) and Simian virus 40 (SV40); an actin promoter, an elongation factor (EF)1α promoter and a heat shock promoter. Examples of promoter expressing the polynucleotide in bacteria (for example, *Escherichia*) include trp promoter, lac promoter, λPL promoter, tac promoter, T3 promoter, T7 promoter and SP6 promoter. Examples of promoter expressing the polynucleotide in yeasts include GAL1 promoter, GAL10 promoter, PH05 promoter, PGK promoter, GAP promoter and ADH promoter. Examples of promoter expressing the polynucleotide in a reaction solution containing RNA polymerase and nucleoside triphosphate include T3 promoter, T7 promoter and SP6 promoter as mentioned above.

If an animal cell, an insect cell or a yeast cell is used as a host cell, or a cell-free protein synthesis solution is used, the expression vector of the present invention may comprise an initiation codon and a stop codon. In this case, the expression vector of the present invention may comprise an enhancer sequence, an untranslated region at the 5' side and the 3' side of a gene encoding a fusion polypeptide of the present invention, a secretion signal sequence, a splicing/joining portion, a polyadenylation site or a replicable unit. If *Escherichia* is used as host cells, the expression vector of the present invention may comprise an initiation codon, a stop codon, a terminator region and a replicable unit. In this case, the expression vector of the present invention may comprise selection markers (for example, a tetracycline resistance gene, an ampicillin resistance gene, a kanamycin resistance gene, a neomycin resistance gene, a dihydrofolate reductase gene) ordinarily and selectively used depending on the purpose.

5. Transformed Host Cell of the Present Invention

Examples of the transformed host cell of the present invention include a (host) cell transformed with an expression vector comprising the nucleotide sequence encoding a cell penetrating peptide of the present invention and a (host) cell transformed with an expression vector comprising a nucleotide sequence encoding a complex of the present invention.

In an embodiment, the transformed host cell of the present invention is a (host) cell transformed with an expression vector of the present invention selected from the group consisting of the following (1) to (3):
(1) a host cell transformed with an expression vector comprising a polynucleotide comprising a nucleotide sequence encoding a peptide consisting of the amino acid sequence of SEQ ID NO: 1;
(2) a host cell transformed with an expression vector comprising a polynucleotide comprising a nucleotide sequence encoding a peptide consisting of the amino acid sequence of SEQ ID NO: 2; and
(3) a host cell transformed with an expression vector comprising a polynucleotide comprising a nucleotide sequence encoding a peptide consisting of the amino acid sequence of SEQ ID NO: 3.

The host cell to be transformed is not particularly limited as long as it adapts to the expression vector to be used and can be transformed with the expression vector and expresses an intended protein. Examples of the host cell to be transformed include various cells such as natural cells or artificially established cells ordinarily used in the technical field of the invention (for example, animal cells (for example, CHO cells), insect cells (for example, Sf9), bacterial cells (for example, *Escherichia*) and yeast cells (for example, *Saccharomyces*, *Pichia*)); preferably, animal cells such as CHO cells, HEK293 cells and NS0 cells, and *Escherichia* can be used.

A method for transforming a host cell is not particularly limited; for example, a calcium phosphate method and electroporation can be used.

6. Method for Producing a Cell Penetrating Peptide of the Present Invention

The cell penetrating peptide of the present invention can be produced by a peptide synthesis method or genetic engineering technique known in the technical field. Examples of the peptide synthesis method include a solid-phase synthesis method (Nature, 2011, Vol. 480, p. 471-479). As the genetic engineering technique, for example, those disclosed in Methods in Enzymol., 1987, Vol. 154, p. 221-533 and Philos. Trans. A Math. Phys. Eng. Sci., 2009, Vol. 367, p. 1705-1726, can be used.

A method for producing the cell penetrating peptide of the present invention may comprise a step of culturing a host cell of the present invention to express a cell penetrating peptide or a step of reacting mRNA, which was synthesized by using an expression vector of the present invention, with a cell-free protein synthesis solution to express the cell penetrating peptide. The method for producing the cell penetrating peptide of the present invention can further comprise a step of recovering an expressed cell penetrating peptide, preferably, followed by isolating and purifying the expressed cell penetrating peptide, in addition to the step of culturing a transformed host cell of the present invention to express a cell penetrating peptide or the step of reacting mRNA, which was synthesized by using an expression vector of the present invention, with a cell-free protein synthesis solution to express the cell penetrating peptide. Examples of the isolation or purification method include a method using solubility such as a salting-out method and a solvent precipitation method; a method using difference in molecular weight such as dialysis, ultrafiltration and gel filtration; a method using electric charge such as ion exchange chromatography and hydroxyapatite chromatography; a method of using specific affinity such as affinity chromatography; a method of using difference in hydrophobicity such as a reversed-phase high-performance liquid chromatography; and a method of using difference in electric point such as isoelectric focusing electrophoresis. Preferably, the cell penetrating peptide accumulated in culture supernatant can be purified by various chromatographic methods.

The host cell transformed can be cultured in accordance with a method known in the art. The culture conditions, such as temperature, pH of a medium and culture time, are appropriately selected. The cell penetrating peptide of the present invention can be produced by culturing the host cell.

Examples of the cell penetrating peptide of the present invention include a cell penetrating peptide produced by the method for producing the cell penetrating peptide of the present invention.

7. Method for Producing a Complex of the Present Invention

A complex of the present invention can be easily produced by those skilled in the art by binding the cell penetrating peptide of the present invention and a functional molecule by a binding method known in the art (Nucleic Acids Res., 2009, Vol. 37, p. 2574-2583).

A method for producing a complex of the present invention comprises a step of binding a functional molecule directly to a cell penetrating peptide by means of a functional group present at an end or within the functional molecule or indirectly via a linker to a cell penetrating peptide, by a chemical binding method. Examples of a chemical binding mode include covalent bonds such as an amide bond, an ester bond, a thioester bond, an ether bond, a thioether bond and an S—S bond; and non-covalent bonds such as an ionic bond, an electrostatic coupling, an intermolecular bond and a hydrogen bond.

If a chemical binding method is employed, the linker used herein is not particularly limited as long as it has a reactive group at the both ends and a structure that can link two molecules. Examples of the reactive group include a maleimide group, an N-succinimide ester group, an epoxy group and an avidin group.

In an embodiment, if the functional molecule is DNA or RNA, the cell penetrating peptide of the present invention and DNA or RNA can be bound by use of, for example, a disulfide bond (FEBS Letters, 2004, Vol. 558, p. 63-68). In an embodiment, the cell penetrating peptide of the present invention and DNA or RNA can be bound via a nucleic acid binding peptide such as protamine (Theranostics, 2017, Vol. 7, p. 2495-2508).

In an embodiment, if the functional molecule is an antibody, the cell penetrating peptide of the present invention and the antibody can be bound by a method known in the art, such as, a maleimidobenzoyloxysuccinimide (MBS) method (NanoBiotechnology Protocols, 2005, Vol. 2, p. 88); a crosslinking method using carbodiimide (Methods in Enzymol., 2012, Vol. 502, p. 102); or a conjugate method (Wong S, Chemistry of Protein Conjugation and Cross-Linking, CRC Press Inc., Boca Raton, 1993).

A complex of the present invention can be easily produced by those skilled in the art by use of a genetic engineering technique known in the art, from a polynucleotide comprising a nucleotide sequence encoding a cell penetrating peptide and a functional molecule of the present invention (Appl. Microbiol. Biotechnol., 2006, Vol. 72, p. 211; Appl. Microbiol. Biotechnol., 2016, Vol. 100, p. 5719-5728).

If a genetic engineering technique is used, the method for producing a complex of the present invention comprise a step of culturing a transformed host cell of the present invention to express the complex or a step of reacting mRNA, which was synthesized by use of an expression vector of the present invention, with a cell-free protein synthesis solution to express the complex. The method for producing a complex of the present invention can further comprise a step of recovering the complex expressed, preferably followed by isolating and purifying, in addition to the aforementioned step, i.e., the step of culturing a transformed host cell of the present invention to express the complex or the step of reacting mRNA, which was synthesized by use of the expression vector of the present invention, with a cell-free protein synthesis solution to express the complex. As an isolation or purification method, for example, the method described in the section <6. Method for producing a cell penetrating peptide of the present invention> can be used.

Examples of the complex of the present invention include a complex produced by the method for producing a complex of the present invention.

8. Pharmaceutical Composition of the Present Invention

Examples of the pharmaceutical composition of the present invention include a pharmaceutical composition comprising a complex of the present invention and a pharmaceutically acceptable excipient. A pharmaceutical composition of the present invention can be prepared by using an excipient ordinarily used in the art, i.e., a pharmaceutical excipient or a pharmaceutical carrier, in accordance with a method ordinarily used therein. Examples of dosage form of the pharmaceutical composition include a parenteral dosage form such as an injection and a drip infusion and can be intravenously or subcutaneously administered. In formulating a pharmaceutical composition, an excipient, a carrier and additives and the like can be used in accordance with each dosage form as long as they are pharmaceutically acceptable.

The amount of the complex of the present invention to be added in the formulation, which varies depending on the degree of symptom and age of the patient, the dosage form of the pharmaceutical composition or the functional molecule, can be, for example, about 0.001 mg/kg to 100 mg/kg.

The pharmaceutical composition of the present invention can be used for preventing and/or treating various diseases in accordance with the function of the functional molecule comprised in the complex of the present invention. For example, if the functional molecule comprised in the complex is a compound, polynucleotide or polypeptide for use in treating a disease, the pharmaceutical composition of the present invention can be used for treating or preventing the disease.

In the present invention, a target disease to be treated or prevented is not particularly limited because the disease can be selected depending on the function of the functional molecule comprised in a complex of the present invention. Examples of the disease include cancers, immune diseases, nervous system diseases, endocrine system diseases and cardiovascular system diseases.

The present invention includes a pharmaceutical composition comprising a complex of the present invention for preventing or treating a disease. Also, the present invention includes a method for treating or preventing a disease, comprising a step of administering a therapeutically effective amount of a complex of the present invention to a patient. Also, the present invention includes a complex of the present invention for use in preventing or treating a disease. Also, the present invention includes a use of a complex of the present invention in manufacturing a pharmaceutical composition for preventing or treating a disease.

In the present invention, examples of the patient are not limited as long as the patient is a mammal, which includes a mouse, a rat, a dog, a pig, a monkey and a human.

The present invention was outlined in the above. Particular examples, which referred to for further understanding, will be provided below. These Examples are provided just as examples and should not be construed as limiting the invention.

EXAMPLES

Experiments using e.g., commercially available kits or reagents were carried out in accordance with the protocol attached to them unless otherwise specified. For convenience sake, a unit (mol/L) of concentration was represented by M. For example, a 1 M aqueous sodium hydroxide solution means a 1 mol/L aqueous sodium hydroxide solution.

In the following Examples, various cell penetrating peptides will be collectively referred to as "CPP" (Cell Penetrating Peptide). In the following Examples, "NTP" refers to a cell penetrating peptide comprising an amino acid sequence, RIFIHFRIGC (SEQ ID NO: 4, International Publication No. WO2008/108505) and a kind of CPP. In the following Examples, a peptide prepared by substituting the 8th amino acid residue I of NTP by Q is expressed to as "NTP (I8Q)" or "NTP8Q"; a peptide prepared by substituting the 10th amino acid residue C from the N terminal of NTP by Q is expressed as "NTP(C10Q)" or "NTP10Q"; and a peptide prepared by substituting the 8th and 10th amino acid residues from the N terminal of NTP both by Q is expressed as "NTP(ICQ2)".

Example 1

Preparation of CPP-EGFP Protein

Proteins (referred to as CPP-EGFP) comprising a cell penetrating peptide (CPP) and EGFP were prepared in accordance with the following method.

(1) Preparation of Expression Plasmid Encoding CPP-EGFP Protein

A polynucleotide (SEQ ID NO: 7) consisting of a nucleotide sequence encoding a polypeptide in which NTP and Glutathione S-transferase (GST) were fused sequentially from the N terminal and comprising EGFP (referred to as NTP-GST-EGFP and consisting of the amino acid sequence of SEQ ID NO: 5), was prepared. To the polynucleotide (SEQ ID NO: 7), a restriction enzyme KpnI site and an initiation codon sequence were added to the 5' end and a stop codon sequence and restriction enzyme NotI site were added to the 3' end to obtain a polynucleotide (SEQ ID NO: 6). The polynucleotide obtained above was treated with restriction enzymes, KpnI and NotI (Takara Bio Inc.) and inserted between KpnI and NotI sites on the multiple cloning site of pEU-E01-MCS plasmid (CellFree Sciences). The expression plasmid obtained in this manner will be referred to as pEU-E01-NTP-GST-EGFP. The expression plasmid was subjected to agarose electrophoresis and sequence analysis ordinarily used. As a result, it was confirmed that a desired DNA construct is cloned.

Subsequently, using pEU-E01-NTP-GST-EGFP as a template and primers consisting of nucleotide sequences of SEQ ID NOs: 8 and 9, inverse PCR (PCR method for amplifying a whole circularized polynucleotide by designing primers from a region of a circular polynucleotide outward) was carried out. By the inverse PCR, a polynucleotide comprising a nucleotide sequence encoding a polypeptide which is prepared by substituting the 8th amino acid residue I of NTP of polypeptide NTP-GST-EGFP by Q (referred to as NTP (I8Q)-GST-EGFP), was synthesized. This was circularized by In-Fusion (registered trademark) HD Cloning Plus kit (Takara Bio Inc.) to prepare an expression plasmid pEU-E01-NTP (I8Q)-GST-EGFP.

Similarly, using pEU-E01-NTP-GST-EGFP as a template and primers consisting of the nucleotide sequences of SEQ ID NOs: 10 and 11, inverse PCR was carried out. By the inverse PCR, a polynucleotide comprising a nucleotide sequence encoding a polypeptide which is prepared by substituting the 10th amino acid residue C of NTP of polypeptide NTP-GST-EGFP by Q (referred to as NTP (C10Q)-GST-EGFP), was prepared. This was circularized by In-Fusion (registered trademark) HD Cloning Plus kit (Takara Bio Inc.) to prepare an expression plasmid pEU-E01-NTP (C10Q)-GST-EGFP.

Further, using pEU-E01-NTP (C10Q)-GST-EGFP as a template and primers consisting of the nucleotide sequences of SEQ ID NOs: 12 and 13, inverse PCR was carried out. By the inverse PCR, a polynucleotide comprising a nucleotide sequence encoding a polypeptide which is prepared by substituting both of the 8th and 10th amino acid residues of NTP of polypeptide NTP-GST-EGFP by Q(referred to as NTP (ICQ2)-GST-EGFP), was prepared. This was circularized by In-Fusion (registered trademark) HD Cloning Plus kit (Takara Bio Inc.) to prepare an expression plasmid pEU-E01-NTP (ICQ2)-GST-EGFP. These expression plasmids were subjected to agarose electrophoresis and sequence analysis ordinarily used. As a result, it was confirmed that desired DNA constructs are obtained.

(2) Preparation of CPP-EGFP Protein

Using the four expression plasmids (pEU-E01-NTP-GST-EGFP, pEU-E01-NTP (I8Q)-GST-EGFP, pEU-E01-NTP (C10Q)-GST-EGFP and pEU-E01-NTP (ICQ2)-GST-EGFP) prepared in the above (1) as templates, CPP-EGFP proteins were prepared and purified in accordance with the following methods.

Using the four expression plasmids (3 μg) prepared in the above (1) and WEPRO7240G Expression Kit (CellFree Sciences), proteins were prepared each in a reaction solution of 0.29 mL in volume. The proteins prepared herein were partly used in Example 5. After the preparation, 0.1% of Empigen (registered trademark) (Sigma) relative to the volume of the reaction solution was added. Further, 100 μL of Glutathione Sepharose 4B (GE Healthcare) saturated with phosphate buffered saline was added. The mixture was shaken at 4° C. for 2 hours. Glutathione Sepharose was collected by centrifugation and suspended in an ice-cold phosphate buffered saline (1 mL) containing 0.1% of Empigen (registered trademark). A centrifugation operation was repeated twice. Glutathione Sepharose collected was suspended in a 1 mL of 150 mM sodium chloride-containing phosphate buffered saline. Glutathione Sepharose was again separated by centrifugation.

Subsequently, in order to extract CPP-EGFP protein bound to Glutathione Sepharose particles, the following operation was carried out. More specifically, 80 μL of a 50 mM tris-HCl buffer (pH 8.0-9.0) containing 30 mM reduced glutathione (Wako) was added to the Glutathione Sepharose mentioned above. The mixture was left to stand at room temperature for 30 minutes while tapping at intervals of several minutes and centrifuged, and the supernatant was recovered. The same operation was repeated twice. CPP-EGFP proteins were collected by recovering the supernatants. To the supernatants, glycerin (Nakarai) was added so as to be a final concentration of 20%. The resultant solutions were stored on ice. The concentrations of each CPP-EGFP protein contained in the supernatants were calculated based on the results of SDS polyacrylamide electrophoresis method and Coomassie brilliant blue staining method in comparison with the results of BSA (Sigma, Fraction V) electrophoresed at the same time.

Example 2

Preparation of CPP-TALE-Activator

A fusion polypeptide comprising CPP, a transcriptional activator-like effector (TALE), which was designed so as to specifically bind to an enhancer of a human TERT gene, and a transcriptional activator (referred to as CPP-TALE-Activator), was prepared by the following method. As a negative control, a fusion polypeptide that comprises TALE and a transcriptional activator but does not comprise CPP (hereinafter also referred to as TALE-Activator) was prepared.

(1) Preparation of Expression Plasmid pEU-E01-GST-NTP-TEV

To the multiple cloning site of expression plasmid pEU-E01-MCS, a polynucleotide (SEQ ID NO: 15) consisting of a nucleotide sequence encoding GST, a polynucleotide (SEQ ID NO: 14) consisting of a nucleotide sequence encoding NTP, and a polynucleotide (SEQ ID NO: 16) consisting of a nucleotide sequence encoding a target peptide (hereinafter referred to as TEV) for TEV protease were inserted in this order from the 5' side.

More specifically, a polynucleotide was synthesized by adding a restriction enzyme EcoRV site to the 5' end of the polynucleotide consisting of the nucleotide sequence of SEQ ID NO: 15 and a restriction enzyme BamHI site to the 3' end thereof. To expression plasmid pEU-E01-MCS, the above polynucleotide was inserted by using EcoRV and BamHI to prepare expression plasmid pEU-E01-GST. Subsequently, a polynucleotide, which comprises a restriction enzyme BamHI site sequence, a nucleotide sequence (SEQ ID NO: 14) encoding NTP, a nucleotide sequence (SEQ ID NO: 16) encoding TEV, a restriction enzyme XhoI site sequence, a restriction enzyme SgfI site sequence, a restriction enzyme PmeI site sequence, a restriction enzyme NotI site sequence and a restriction enzyme SalI site sequence in this order from the 5' end side, was prepared. Cytosine was inserted between the XhoI site and the SgfI site of above polynucleotide in order to match the frame of the encoded amino acid sequence. The polynucleotide mentioned above was inserted into expression plasmid pEU-E01-GST by using BamHI and SalI. Thereafter, inverse PCR was carried out by using primers consisting of the nucleotide sequences of SEQ ID NOs: 17 and 18 to prepare expression plasmid pEU-E01-GST-NTP-TEV.

(2) Preparation of Plasmid pEU-E01-GST-NTP-TEV-ΔTALE-VP64V

The polynucleotide consisting of the nucleotide sequence of SEQ ID NO: 19 (comprising a nucleotide sequence encoding a part of TALE and a nucleotide sequence encoding VP64 (SEQ ID NO: 21) and referred to as ΔTALE-VP64V) was incorporated into immediately downstream of the nucleotide sequence encoding TEV of expression plasmid pEU-E01-GST-NTP-TEV prepared in the above (1) by using In-Fusion (registered trademark) HD Cloning Plus kit to obtain plasmid pEU-E01-GST-NTP-TEV-ΔTALE-VP64V. Since valine was added to the C terminal of VP64, the name of the plasmid was ended by V.

(3) Preparation of TALE Targeting to Human TERT Gene

A surrounding sequence serving as a telomerase subunit of a human TERT gene (Accession No. AH007699.2) was searched using Ensembl genome browser, which is database open to public. A nucleotide sequence from nucleotide positions 49444 to 49461 in Accession No. AH007699.2 (the nucleotide sequence of SEQ ID NO: 20) was selected as a target nucleotide sequence of TALE from a gene region, which presumably acts as an enhancer, on about 40,000 bps downstream of the transcription-initiation site of the gene. By a method known in the art (Platinum Gate TALEN construction protocol (Yamamoto lab) Ver. 1.0, the polynucleotide comprising a nucleotide sequence encoding DNA-binding polypeptide that designed so as to specifically bind to the nucleotide sequence of SEQ ID NO: 20 (polynucleotide comprising a nucleotide sequence from nucleotide positions 429 to 2064 in SEQ ID NO: 22) was prepared. Then, using T4 DNA Ligase (Quick Ligation Kit: New England Biolabs), the polynucleotide consisting of the nucleotide sequence from nucleotide positions 435 to 889 of SEQ ID NO: 19, which is comprised in plasmid pEU-E01-GST-NTP-TEV-ΔTALE-VP64V prepared in the above (2), was replaced by the polynucleotide consisting of the nucleotide sequence from nucleotide positions 429 to 2064 of SEQ ID NO: 22. In this manner, a plasmid comprising a polynucleotide (consisting of the nucleotide sequence of SEQ ID NO: 22) consisting of a nucleotide sequence encoding a DNA binding polypeptide consisting of the amino acid sequence of SEQ ID NO: 23 (also referred to as TALE_TERT-1), was obtained. The amino acid sequence from amino acid positions 7 to 784 of SEQ ID NO: 23 is a polypeptide portion comprising a DNA binding repeat portion and thymine-binding portion of TALE, which is designed so as to bind to the nucleotide sequence of SEQ ID NO: 20. The plasmid will be referred to as pEU-E01-GST-NTP-TEV-TALE-VP64V.

(4) Preparation of Expression Plasmid Encoding CPP-TALE-Activator

PCR using primers consisting of nucleotide sequences of SEQ ID NOs: 24 and 25 was carried out by using expression plasmid pEU-E01-GST-NTP-TEV-TALE-VP64V prepared in the above (3) as a template and PrimeSTAR (registered trademark) Max DNA Polymerase (Takara Bio Inc.). In this manner, a polynucleotide comprising a nucleotide sequence encoding TALE and VP64 and having a SgfI site sequence added to the 5' end side and a NotI site sequence added to the 3' end side, was prepared. The polynucleotide will be referred to as TALE-VP64. The polynucleotide TALE-VP64 was cleaved with SgfI and NotI and inserted between restriction enzyme sites SgfI and NotI of expression plasmid pEU-E01-GST-NTP-TEV prepared in the above (1) to prepare expression plasmid pEU-E01-GST-NTP-TEV-TALE-VP64.

Using SP-dCas9-VPR (Addgene) as a template, PrimeSTAR (registered trademark) Max DNA Polymerase, and primers consisting of nucleotide sequences of SEQ ID NOs: 26 and 27, PCR was carried out. In this manner, CGCGCGTCAGCCAGC (SEQ ID NO: 29) was added to the 5' end side of a polynucleotide encoding VPR (SEQ ID NO: 28) and GTTTAAACTGCGGCC (SEQ ID NO: 30) was added to the 3' end side. The polynucleotide will be referred to as VPR-PCR.

Subsequently, using expression plasmid pEU-E01-GST-NTP-TEV-TALE-VP64 as a template and primers consisting of nucleotide sequences of SEQ ID NOs: 31 and 32, PCR was carried out. In this manner, the polynucleotide in which the nucleotide sequence encoding VP64 was removed, and CGCGCGTCAGCCAGC (SEQ ID NO: 29) was added to the 3' side and GTTTAAACTGCGGCC (SEQ ID NO: 30) was added to the 5' side, was prepared. The polynucleotide will be referred to as pEU-E01-GST-NTP-TEV-TALE-PCR.

Using In-Fusion (registered trademark) HD Cloning Plus kit, pEU-E01-GST-NTP-TEV-TALE-PCR and VPR-PCR were ligated in a molar ratio of 1:10. In this manner, an expression plasmid encoding transcriptional activator VPR was prepared. The expression plasmid will be referred to as pEU-E01-GST-NTP-TEV-TALE-VPR. The expression plasmid was subjected to agarose electrophoresis and sequencing ordinarily performed. As a result, it was confirmed that a desired construct is cloned.

Subsequently, pEU-E01-GST-NTP-TEV-TALE-VPR was treated with restriction enzymes AsiSI (New England Biolabs Inc.) and SwaI (Takara Bio Inc.).

Polynucleotides consisting of nucleotide sequences of SEQ ID NO: 33, 34 and 35, respectively, were synthesized and each polynucleotide was treated with restriction enzymes, AsiSI and SwaI. Agarose gel electrophoresis was carried out, and about 340 base polynucleotide fragments were cut out and purified by FastGene Gel/PCR Extraction kit (NIPPON Genetics, FG91202). The polynucleotide fragments were ligated to expression plasmid pEU-E01-GST-NTP-TEV-TALE-VPR cleaved with AsiSI and SwaI by use of T4 DNA ligase (Takara Bio Inc.). The plasmid obtained by ligation was introduced into Stbl competent cells (New England Biolabs Inc.) with a heat treatment and cultured on 100 μg/mL ampicillin (Sigma)-containing LB medium agar plate (consisting of a solution containing 10 g/L Bacto Trypton (Becton Dickinson), 5 g/L Bacto Yeast Extract (Becton Dickinson) and a 10 g/L aqueous sodium chloride (Wako), and 1.5% agarose (Wako)) (hereinafter referred to as LA plate) at 30° C., overnight. From the colonies generated, a plasmid was purified. In this manner, pEU-E01-GST-NTP (ICQ2)-TALE-VPR, pEU-E01-GST-NTP8Q-TALE-VPR and pEU-E01-GST-NTP10Q-TALE-VPR, in which the polynucleotide region encoding NTP of expression plasmid pEU-E01-GST-NTP-TEV-TALE-VPR was replaced by polynucleotides encoding SEQ ID NOs: 1, 2 and 3, respectively, were obtained. Sequence analysis was carried out. As a result, it was confirmed that the above constructs are properly prepared.

(5) Preparation of CPP-TALE-Activator

Using expression plasmids (pEU-E01-GST-NTP-TEV-TALE-VPR, pEU-E01-GST-NTP8Q-TALE-VPR, pEU-E01-GST-NTP10Q-TALE-VPR and pEU-E01-GST-NTP (ICQ2)-TALE-VPR) encoding CPP-TALE-Activators prepared in the above (4) as templates, CPP-TALE-Activators were prepared by using WEPRO7240G Expression Kit in accordance with the following method and then purified.

The proteins were prepared in a reaction solution (0.29 mL) using CPP-TALE-Activator expression plasmid (1 μg) prepared in the above (4) (the amount of NTP-TALE-VPR expression plasmid used in Example 4 (2) was 3 μg) by using WEPRO7240G Expression Kit. After preparation, 0.1% Empigen relative to the volume of the reaction solution was added. Further, 60 μL of Glutathione Sepharose 4B (100 μL to the reaction solution for preparing NTP-TALE-VPR used in Example 4 (2)) saturated with phosphate buffered saline, was added. The mixture was shaken at 4° C. for 2 hours. Glutathione Sepharose was collected by centrifugation and suspended in an ice-cold phosphate buffered saline (1 mL). Centrifugation operation was repeated twice. The Glutathione Sepharose was suspended in 1 mL of 150 mM sodium chloride-containing phosphate buffered saline. Glutathione Sepharose was again separated by centrifugation.

Subsequently, in order to extract CPP-TALE-Activator bound to Glutathione Sepharose, the following operation was carried out. More specifically, 80 μL of 50 mM tris-HCl buffer (pH 8.0-9.0) containing 30 mM reduced glutathione (Wako) was added to the Glutathione Sepharose. After shaking at room temperature for one minute, the supernatant was collected by centrifugation. The same operation was repeated twice. CPP-TALE-Activator was obtained by recovering the supernatant. The concentration of CPP-TALE-Activator Protein contained in the supernatant recovered was calculated based on the results of SDS polyacrylamide electrophoresis method and Coomassie brilliant blue staining method in comparison with the results of BSA electrophoresed at the same time.

The polypeptides obtained from pEU-E01-GST-NTP-TEV-TALE-VPR, pEU-E01-GST-NTP8Q-TALE-VPR, pEU-E01-GST-NTP10Q-TALE-VPR and pEU-E01-GST-NTP (ICQ2)-TALE-VPR will be referred to as NTP-TALE-VPR, NTP8Q-TALE-VPR, NTP10Q-TALE-VPR and NTPICQ2-TALE-VPR, respectively.

(6) Preparation of TALE-Activator

As a negative control in Example 4, an expression plasmid encoding a fusion polypeptide which comprises TALE and VPR but does not comprise CPP (referred to as TALE-VPR) was prepared.

Using expression plasmid pEU-E01-GST-NTP-TEV-TALE-VPR prepared in the above (4) as a template, PrimeSTAR (registered trademark) Max DNA Polymerase, and primers consisting of nucleotide sequences of SEQ ID NOs: 36 and 37, Inverse PCR was carried out. In this manner, the polynucleotide in which the nucleotide sequences encoding NTP and TEV alone was removed from the expression plasmid pEU-E01-GST-NTP-TEV-TALE-VPR, was synthesized. This polynucleotide was allowed to self-ligate by use of In-Fusion (registered trademark) HD Cloning Plus kit to prepare expression plasmid pEU-E01-GST-TALE-VPR. Agarose electrophoresis and sequencing were carried out. As a result, it was confirmed that a desired construct is obtained.

TALE-VPR was prepared and purified in the same manner as described in "(5) Preparation of CPP-TALE-Activator" by using expression plasmid pEU-E01-GST-TALE-VPR as a template and WEPRO7240G Expression Kit.

Example 3

Cell Membrane Penetration Experiment (EGFP experiment)

Human lung cancer-derived cells A549 (ATCC (registered trademark) CCL-185) were suspended in RPMI medium (Thermo Fisher Scientific) containing a 10% fetal bovine serum (GE Healthcare) and 1% penicillin-streptomycin (Thermo Fisher Scientific), and seeded in a 96-well culture plate (Iwaki Glass) at a density of $0.2 \times 10^4$ cells/100 µL/well. After culture for 36 hours, 3-3.7 µL each of NTP-GST-EGFP, NTP (I8Q)-GST-EGFP, NTP (C10Q)-GST-EGFP and NTP (ICQ2)-GST-EGFP prepared in Example 1 was added to each well so as to be a final concentration 30 nM. As a negative control, 3 µL of EGFP (Funakoshi) adjusted in concentration with phosphate buffered saline was added so as to be a final concentration of 30 nM. As a control, 3 µL of phosphate buffered saline alone was added. After 24 hours, the cells in each well were washed with 100 µL of phosphate buffered saline. The above medium (100 µL) was added, the cells emitting green fluorescence of GFP were observed by using an all-in-one fluorescence microscope BZ-8100 (KEYENCE) at 10× magnification and the number of the cells were counted. The measurement manner was as follows. An image of a single viewing field under the microscope was taken and the number of cells emitting green fluorescence was counted. The number of cells was divided by the total number of cells in the same viewing field. This operation was repeated three times to obtain an average. The numbers of cells into which the above fusion proteins penetrated and functioned there were compared.

The results are shown in FIG. 1. When NTP-GST-EGFP, NTP (I8Q)-GST-EGFP, NTP (C10Q)-GST-EGFP and NTP (ICQ2)-GST-EGFP were compared to the control and EGFP, it was confirmed that the numbers of GFP positive cells are large. From the above results, it was demonstrated that the peptides consisting of the amino acid sequences of SEQ ID NOs: 1, 2 and 3 have cell penetration capability.

Example 4

(1) Measurement of Intracellular Human TERT mRNA Expression Level in the Case of Adding CPP-TALE-Activator CPP-TALE-Activators (NTP-TALE-VPR, NTPICQ2-TALE-VPR, NTP8Q-TALE-VPR and NTP10Q-TALE-VPR) prepared in Example 2 were dialyzed against OPTIMEM medium (Thermo Fisher Scientific) at 4° C. for 3 hours in Microdialysis column (Tommy). After purification, the concentration was 50 nM.

Human umbilical cord matrix-derived mesenchymal stem cells (PromoCell C-12971, hereinafter referred to as UC-MSC) were suspended in MSCGM-CD mesenchymal stem cell growth medium BulletKit (Lonza Japan, 00190632), seeded in 96-well collagen I coated transparent culture plate (Corning) at a density of $0.4 \times 10^4$ cells/100 µL/well and incubated in a $CO_2$ incubator set at a $CO_2$ concentration of 5% and 37° C. for 12 hours. Thereafter 240 nM of each CPP-TALE-Activator was added so as to be a final concentration of 0.25, 1, 3, 10 and 30 nM, respectively. The cells were incubated in a $CO_2$ incubator set at a $CO_2$ concentration of 5% and 37° C. for 24 hours. As a control, a well comprising no CPP-TALE-Activator was prepared.

After 24 hours, the intracellular human TERT mRNA expression level was measured in accordance with the following method. The culture supernatant was removed from each well of the cultured cells and the cells were washed once with ice-cold phosphate buffered saline. Thereafter, 25 µL of a lysis solution (a solution mixture of Lysis solution (24.5 µL) and DNase I (0.5 µL)) provided in Ambion (registered trademark) Power SYBR Cells-to-CT™ kit (Thermo Fisher Scientific) was added to each well and mixed with the cells. After being left to stand at room temperature for 5 minutes, Stop solution (2.5 µL) provided in the above kit was added to each well and the cells were left to stand at room temperature for 2 minutes. In this manner, a cell lysate containing RNA extracted from the cells was obtained.

Using the above cell lysate as a template and reverse transcriptase provided in the above kit, cDNA was prepared from RNA in accordance with the protocol. Subsequently, using the following primers and Power SYBR Green PCR Master Mix provided in the above kit, Real Time-PCR was carried out by CFX96 Touch real time PCR Analysis system (Bio-Rad) and human TERT mRNA level was measured. The mRNA level of human actin beta (ACTB) was measured as an endogenous control (gene). The human TERT mRNA level was divided by the human ACTB mRNA level and the obtained value was used as human TERT mRNA relative expression level. The relative expression level of human TERT mRNA of the control was regarded as 1, the relative expression levels of human TERT mRNAs of each group were calculated. Three wells per sample were used for calculation.

As TERT Forward primer and TERT Reverse primer, the primers consisting of nucleotide sequences of SEQ ID NOs: 38 and 39 were used, respectively. Also, as ACTB Forward primer and ACTB Reverse primer, the primers consisting of nucleotide sequences of SEQ ID NOs: 40 and 41 were used, respectively.

As shown in FIG. 2, the intracellular human TERT mRNA level of a CPP-TALE-Activator addition group was, at most, 19 times as high as that of no addition group UC-MSC.

(2) Measurement of Intracellular Human TERT mRNA Expression Levels of the Cases of Adding NTP-TALE-VPR and TALE-VPR UC-MSC were suspended in DMEM medium (Thermo Fisher Scientific, hereinafter referred to as 20% FCS-DMEM medium) containing a 20% fetal calf serum (GE Healthcare), 1% penicillin-streptomycin (Thermo Fisher Scientific) and 2 mM L-Glutamine (Thermo Fisher Scientific), seeded in a 96-well transparent culture plate (Iwaki Glass) at a density of $0.4 \times 10^4$ cells/100 µL/well and left to stand in a $CO_2$ incubator set at a $CO_2$ concentration of 5% and 37° C. for 12 hours. NTP-TALE-VPR adjusted in concentration so as to be 300 nM with 20% FCS-DMEM medium was added to wells so as to be a final concentration in well of 0.25 nM. Also, a negative control TALE-VPR adjusted in concentration so as to be 300 nM with 20% FCS-DMEM medium and comprising no CPP was added to wells so as to be a final concentration (in well) of 0.25, 1, 3, 10 and 30 nM. These were left to stand at 37° C., in an incubator having a $CO_2$ concentration of 5% for 24 hours. As a control, a well comprising no substance added therein was prepared. After washing was made twice with ice-cold phosphate buffered saline (100 µL), the culture plate was treated with liquid nitrogen to freeze cells.

The above culture plate was thawed by placing it on ice; at the same time, 30 µL of a lysis solution (solution mixture of Lysis solution (29.7 µL) and DNase I (0.3 µL)) provided in TaqMan (registered trademark) Gene Expression Cells-to-CT™ kit (Thermo Fisher Scientific) was added to each well and mixed with the cells. After being left to stand at room temperature for 5 minutes, Stop solution (3 µL)

provided in the above kit was added to each well and the cells were left to stand at room temperature for 5 minutes. In this manner, a cell lysate containing RNA extracted from the cells was obtained.

Using the above cell lysate as a template and TaqMan (registered trademark) Fast Advanced Master Mix (Thermo Fisher Scientific), Real Time-PCR was carried out by using 7900HT Fast Real Time PCR System (Applied Biosystems), and human TERT mRNA level was measured. As an endogenous control, human ACTB mRNA level was measured. The human TERT mRNA level was divided by the human ACTB mRNA level and the obtained value was used as human TERT mRNA relative expression level. The relative expression level of human TERT mRNA of the control was regarded as 1, the relative expression levels of human TERT mRNAs of each group were calculated. Three wells per sample were used for calculation.

As the primer set of human TERT, TERT FAM (Applied Biosystems, Hs00972648_g1) was used. As the primer set of human ACTB, ACTB VIC (Applied Biosystems, Hs99999903_m1) was used.

As shown in FIG. 3, in the TALE-VPR addition group, a remarkable increase in intracellular human TERT mRNA level was not observed, unlike the NTP-TALE-VPR addition group. As a result of the above (1) and (2), it was found that increase of intracellular human TERT mRNA level by CPP-TALE-Activator varies depending on cell membrane penetration ability of CPP. In the foregoing, it was demonstrated that peptides consisting of amino acid sequences of SEQ ID NOs: 1, 2 and 3 have cell membrane penetration ability.

From the results of Examples 3 and 4, it was demonstrated that the peptide of the present invention can deliver a functional molecule bound to the peptide into the inside of cells. From the results, it was also demonstrated that the complex of the present invention can penetrate into the inside of cells. It was further demonstrated that the functional molecules and the complex of the present invention penetrated into the inside of cells by the peptide of the present invention exert the function thereof within the cell.

Example 5

GFP-F SEC Analysis of CPP-EGFP Protein

In order to study the aggregation of CPP-EGFP proteins prepared in Example 1, soluble fractions of the each protein were analyzed by GFP-FSEC method.

The GFP-FSEC method is a method for detecting a GFP fusion protein by use of high performance liquid chromatography (HPLC) equipped with a fluorescence detector.

As equipment for HPLC, an HPLC column, an auto sampler (SIL-HTC, Shimadzu Corporation), a pump for liquid delivery (LC-10ADVP, Shimadzu Corporation), a degasser (DGU-14A, Shimadzu Corporation), a column oven (CTO-10ACVP, Shimadzu Corporation) and a fluorescence detector (RF-10AXL, Shimadzu Corporation) are mentioned. As the HPLC column, ENrich™SEC650, 10×300 column (Bio-Rad) was used. The Detector was set at Ex 488 nm and Em 508 nm. As the chromatogram display software and sigmoid calculation software, LCSolutions ver. 1.25 (Shimadzu Corporation) and FSECplotter2 (Open source software, TaizoAyase, https://libraries.io/github/TaizoAyase/FSECplotter2 (Oct. 18, 2018)) were used, respectively.

To each crude sample 25 µL (containing 5 µg of CPP-EGFP protein) of CPP-EGFP proteins prepared in Example 1, i.e., NTP-GST-EGFP, NTP (I8Q)-GST-EGFP, NTP (C10Q)-GST-EGFP and NTP (ICQ2)-GST-EGFP, phosphate buffer (75 µL) was added. After mixed in a 1.5 mL-micro tube, the samples were centrifuged at 4° C. for 15 minutes at a rotation number of 15,000 per minute to separate soluble fractions. The soluble fractions were separately transferred to 96-well plates and each sample (50 µL) was added sequentially to a column equilibrated with a phosphate buffer. Gel filtration chromatography was carried out at a flow rate of 1.0 mL/min. The amounts of GFP fusion proteins detected were plotted along with molecular weight by sigmoid calculation software FSECplotter2 to make a graph.

The results are shown in FIG. 4A and FIG. 4B. NTP-GST-EGFP was not virtually detected in a soluble fraction (FIG. 4B). In contrast, in the cases of NTP (I8Q)-GST-EGFP, NTP (C10Q)-GST-EGFP and NTP (ICQ2)-GST-EGFP, peaks of remarkable low molecular weights were detected. Accordingly, it was confirmed that solubilities of NTP (C10Q)-GST-EGFP, NTP (I8Q)-GST-EGFP and NTP (ICQ2)-GST-EGFP were improved compared to NTP-GST-EGFP.

In the detection results of the Examples, two peaks in a high molecular weight and a low molecular weight were observed (FIG. 4A (1)-(4)). The peak of the low molecular weight represents a CPP-EGFP protein; whereas, the peak of the high molecular weight represents an aggregate. When the ratio of proteins of these peaks were compared, it was confirmed that the peaks of the high molecular weight and low molecular weight in the case of NTP-GST-EGFP are a similar level; whereas, the peak of low molecular weight increases sequentially in the order of NTP (ICQ2)-GST-EGFP, NTP (I8Q)-GST-EGFP and NTP (C10Q)-GST-EGFP, and the peaks of high molecular weight are low.

From the above results, it was demonstrated that, in the proteins NTP (C10Q)-GST-EGFP, NTP (I8Q)-GST-EGFP and NTP (ICQ2)-GST-EGFP compared to NTP-GST-EGFP, formation of a high molecular weight aggregate was reduced.

GST-EGFP portions of the above 4 types of fusion proteins have the same structure. From this, in cell penetrating polypeptide NTP (I8Q), NTP (C10Q) and NTP (ICQ2) of the present invention, compared to NTP, it was confirmed that solubility is improved by reducing aggregation of a fusion protein, with the result that properties useful for producing and purifying the fusion proteins can be given.

INDUSTRIAL APPLICABILITY

The cell penetrating peptide of the present invention is expected to be useful for delivering functional molecules into the inside of cells. The complex of the present invention is expected to be useful as a constitutional component of various reagents and pharmaceutical compositions. Also, the method for producing the polynucleotide, expression vector, host cell transformed and protein of the present invention are expected to be useful for producing the cell penetrating peptide and the complex.

Free Text of Sequence Listing

In numeric identifier <223> in the following sequence listing, the description of "Artificial Sequence" will be described. More specifically, the amino acid sequences of SEQ ID NOs: 1, 2, 3 and 4 are amino acid sequences of NTP (ICQ2), NTP (I8Q), NTP (C10Q) and NTP, respectively. The amino acid sequence of SEQ ID NO: 5 is the amino acid sequence of NTP-GST-EGFP. The nucleotide sequence of SEQ ID NO: 6 is the nucleotide sequence of the polynucleotide prepared by adding a restriction enzyme KpnI site and an initiation codon sequence to the 5' end of the polynucleotide consisting of the nucleotide sequence of SEQ ID NO: 7 and adding a stop codon sequence and restriction enzyme NotI site to the 3' end thereof. The nucleotide sequence of SEQ ID NO: 7 is a nucleotide sequence encoding NTP-GST-EGFP. The nucleotide sequences of SEQ ID NOs: 8-13, 17, 18, 24-27, 31, 32 and 36-41 are the nucleotide sequences of primers. The nucleotide sequence of SEQ ID NO: 14 is the nucleotide sequence encoding NTP. The nucleotide sequence of SEQ ID NO: 16 is the nucleotide sequence encoding TEV. The nucleotide sequence of SEQ ID NO: 19 is the nucleotide sequence encoding ΔTALE-VP64. The amino acid sequence of SEQ ID NO: 21 is the amino acid sequence of VP64. The nucleotide sequence of SEQ ID NO: 22 is the nucleotide sequence of TALE_TERT-1. The amino acid sequence of SEQ ID NO: 23 is the amino acid sequence of TALE_TERT-1 encoded by the nucleotide sequence of SEQ ID NO: 22. The amino acid sequence of SEQ ID NO: 28 is the amino acid sequence of VPR. The nucleotide sequences of SEQ ID NOs: 29 and 30 are the nucleotide sequences of 5' end side and 3' end side of VPR-PCR, respectively. The nucleotide sequence of SEQ ID NO: 33 is the nucleotide sequence of a polynucleotide comprising the nucleotide sequence encoding NTP (ICQ2). The nucleotide sequence of SEQ ID NO: 34 is the nucleotide sequence of a polynucleotide comprising the nucleotide sequence encoding NTP (I8Q). The nucleotide sequence of SEQ ID NO: 35 is the nucleotide sequence of a polynucleotide comprising the nucleotide sequence encoding NTP (C10Q).

The invention claimed is:

1. A complex comprising the peptide consisting of the amino acid sequence of SEQ ID NO: 1 and a functional molecule, wherein the functional molecule is selected from the group consisting of polynucleotides, polypeptides, lipids, carbohydrates, magnetic particles and liposomes.

* * * * *